US012661526B2

(12) United States Patent

Burnett et al.

(10) Patent No.: US 12,661,526 B2

(45) Date of Patent: Jun. 23, 2026

(54) BRACHYTHERAPY DEVICE

(71) Applicant: Margin-Clear Pty Ltd, Melbourne (AU)

(72) Inventors: David Burnett, Melbourne (AU); David James, Melbourne (AU); Geoffrey Spinks, Melbourne (AU); Aida Shoushtari Zadeh Naseri, Melbourne (AU); Ashley Walker, Melbourne (AU); Aleksandra Bjelosevic, Melbourne (AU); Krishant Deo, Melbourne (AU)

(73) Assignee: Margin-Clear Pty Ltd, Melbourne (AU)

( * ) Notice: Subject to any disclaimer, the term of this patent is extended or adjusted under 35 U.S.C. 154(b) by 0 days.

(21) Appl. No.: 19/187,251

(22) Filed: Apr. 23, 2025

(65) Prior Publication Data

US 2025/0249284 A1 Aug. 7, 2025

Related U.S. Application Data

(63) Continuation of application No. PCT/AU2024/051008, filed on Sep. 20, 2024.

(30) Foreign Application Priority Data

Sep. 20, 2023 (AU) ................................ 2023903027

(51) Int. Cl.
  *A61N 5/10* (2006.01)
  *A61F 13/02* (2024.01)
  (Continued)

(52) U.S. Cl.
  CPC ........ *A61N 5/1029* (2013.01); *A61F 13/0289* (2013.01); *A61K 51/1279* (2013.01);
  (Continued)

(58) Field of Classification Search
  CPC .. A61N 5/1007; A61N 5/1028; A61N 5/1029;
        A61N 2005/1011; A61N 5/1014;
  (Continued)

(56) References Cited

U.S. PATENT DOCUMENTS 3,351,049 A * 11/1967 Lawrence ............. A61M 31/00
                                                     252/644
5,871,708 A 2/1999 Park et al.
  (Continued)

FOREIGN PATENT DOCUMENTS

CA 2171124 C * 1/2001 ......... A61K 51/1279
EP 1008995 * 6/2000 ........... A61N 5/1027
  (Continued)

OTHER PUBLICATIONS

Häfeli et al., "Fibrin glue system for adjuvant brachytherapy of brain tumors with 188Re and 186Re-labeled microspheres," European Journal of Pharmaceutics and Biopharmaceutics 65(3):282-288, Mar. 2007 [Published online Nov. 10, 2006]. (7 pages).
  (Continued)

*Primary Examiner* — Carrie R Dorna
(74) *Attorney, Agent, or Firm* — Seed Intellectual Property Law Group LLP

(57) ABSTRACT

The disclosure relates to an improved brachytherapy device, methods of preparation, and uses thereof. More particularly, a flexible bioresorbable brachytherapy device is provided for application on a wound site in a subject. The device includes a sealed radioactive source having opposite first and second sides, wherein the sealed radioactive source includes a radioactive component comprising a plurality of radio-isotope particles dispersed within a carrier. A barrier surrounds the radioactive component providing the sealed radioactive source, wherein the barrier functions as a barrier, when implanted at the wound site, providing the sealed
  (Continued)

radioactive source for at least six half-lives of the plurality of radio-isotope particles. A bioresorbable shield located on the first side of the sealed radioactive source is configured to shield radioactivity when implanted at the wound site for at least six half-lives of the plurality of radio-isotope particles.

14 Claims, 14 Drawing Sheets

(51) Int. Cl.
    *A61K 51/12*        (2006.01)
    *A61B 17/00*       (2006.01)

(52) U.S. Cl.
    CPC ............... *A61B 2017/00004* (2013.01); *A61N 2005/1094* (2013.01)

(58) Field of Classification Search
    CPC .......... A61N 5/1015; A61N 2005/1024; A61N 2005/1092; A61L 15/64; A61F 13/0289
    See application file for complete search history.

(56)            References Cited

U.S. PATENT DOCUMENTS

| | | | |
|---|---|---|---|
| 6,149,889 | A | 11/2000 | Chin et al. |
| 6,248,057 | B1 | 6/2001 | Mavity et al. |
| 6,575,887 | B1 | 6/2003 | Schrayer |
| 6,749,554 | B1 | 6/2004 | Snow et al. |
| 9,486,642 | B2 | 11/2016 | Cipriani et al. |
| 2001/0044567 | A1 | 11/2001 | Zamora et al. |
| 2001/0051766 | A1* | 12/2001 | Gazdzinski ............ A61B 10/02 |
| | | | 606/1 |
| 2002/0055667 | A1 | 5/2002 | Mavity et al. |
| 2003/0204125 | A1 | 10/2003 | Brauckman et al. |
| 2003/0233136 | A1 | 12/2003 | Williams et al. |
| 2006/0116696 | A1 | 6/2006 | Odermatt et al. |
| 2006/0269475 | A1 | 11/2006 | Ryu et al. |
| 2007/0016179 | A1 | 1/2007 | Francescatti et al. |
| 2015/0104380 | A1 | 4/2015 | Chang et al. |
| 2015/0306420 | A1* | 10/2015 | Strauss ............ A61B 17/12186 |
| | | | 600/7 |
| 2020/0188691 | A1 | 6/2020 | Sarazin et al. |
| 2020/0276007 | A1 | 9/2020 | Musara |
| 2020/0397929 | A1* | 12/2020 | Burnett .................... A61N 5/00 |

FOREIGN PATENT DOCUMENTS

| | | | | |
|---|---|---|---|---|
| EP | 1008995 | A1 * | 6/2000 | ........... A61N 5/1027 |
| EP | 1536746 | B1 | 5/2013 | |
| WO | 9719706 | A1 | 6/1997 | |
| WO | 02100480 | A2 | 12/2002 | |
| WO | 2007052267 | A2 | 5/2007 | |
| WO | 2007106531 | A1 | 9/2007 | |
| WO | 2008024959 | A2 | 2/2008 | |
| WO | 2009029224 | A1 | 3/2009 | |
| WO | 2009134431 | A1 | 11/2009 | |
| WO | 2011084465 | A2 | 7/2011 | |
| WO | 2017173352 | A1 | 10/2017 | |
| WO | 2018009839 | A1 | 1/2018 | |
| WO | 2019169445 | A1 | 9/2019 | |
| WO | WO-2022201130 | A1 * | 9/2022 | ............. A61K 35/60 |

OTHER PUBLICATIONS

International Preliminary Report on Patentability, dated Jun. 16, 2020, for International Patent Application No. PCT/AU2019/050201. (41 pages).

International Search Report and Written Opinion, dated Dec. 10, 2024, for International Patent Application No. PCT/AU2024/051008. (11 pages).

International Search Report, dated Mar. 26, 2019, for International Patent Application No. PCT/AU2019/050201. (8 pages).

International-Type Search Report (PCT Article 15(5)), dated Dec. 18, 2018, for Australian Provisional Patent Application No. 2018900745. (16 pages).

Kaplan et al., "A comparison of the precision of seeds deposited as loose seeds versus suture embedded seeds: A randomized trial," Brachytherapy 3(1):7-9, 2004. (3 pages).

Karsh et al., "Absorbable Hydrogel Spacer Use in Prostate Radiotherapy: A Comprehensive Review of Phase 3 Clinical Trial Published Data," Urology 115:39-44, May 2018. (6 pages).

Lee et al., "Surface coating for prevention of metallic seed migration in tissues," Medical Physics 42(6):2805-2812, Jun. 2015. (9 pages).

Qu et al., "Encapsulation of isotope on novel ß-emitting poly(ethylene terephthalate) surfaces," Journal of Biomedical Materials Research 57(4):619-623, Dec. 15, 2001. (5 pages).

Rahman et al. "Adjuvant Chemotherapy for Brain Tumors Delivered via a Novel Intra-Cavity Moldable Polymer Matrix," PLOS One 8(10), Oct. 2013. (12 pages).

Salgueiro et al., "Bioevaluation of 32P patch designed for the treatment of skin diseases," Nuclear Medicine and Biology 35(2):233-237, Feb. 2008 [Published online Nov. 19, 2007]. (5 pages).

Supplementary European Search Report, dated Oct. 29, 2021, for European Patent Application No. 19764767. (1 page).

\* cited by examiner

227A

223

223A

227

BRACHYTHERAPY DEVICE

BACKGROUND

Technical Field

The disclosure relates to an improved brachytherapy device, methods of preparation, and uses thereof.

Description of the Related Art

This application claims priority from Australian provisional application no. 2023903027 the entire contents of which is hereby incorporated by reference in its entirety.

Neoplasia is the uncontrolled, abnormal growth of cells or tissues in the body. A neoplasm can be benign (noncancerous) or malignant (cancerous).

Cancer is a disease of the cells that impacts multiple body organs and affects a large number of people throughout the world. When normal mechanisms for regulating the growth of cells in the body are disturbed, cells can begin to grow in an uncontrolled fashion. A cancer develops when normal cells in the body begin to develop an abnormal growth pattern, and do not undergo the normal cell lifecycle including cell death. The uncontrolled rapid growth, and invasion of normal tissue by abnormal cells is the definition of malignant cancer. Cancer cells may undergo metastasis whereby they detach from their primary site and travel to other parts of the body where they begin to grow new tumor deposits.

Treatments for cancer can include surgery, chemotherapy, and radiation therapy or combinations thereof. Surgery is usually the treatment of choice for many solid organ cancers if the cancer appears localized to an organ, and initial work up of a patient to determine whether the tumor is removable by surgical means. Some cancers are amenable to surgical resection of metastatic deposits, such as colorectal, melanoma, and neuroendocrine tumors.

In surgical removal of a cancerous tumor, it is important to completely remove or destroy all the malignant cells. Surgical removal of cancer involves cutting out the tumor or tumors, including a margin of normal tissue around the cancer to ensure the entire disease is excised. This often includes removal of the lymph nodes to which the primary tumor may spread. Generally, a pathological examination of the resection margin of the tissue that is removed is employed at the time of surgery to ensure that the tumor has been completely removed.

One of the most feared complications of major cancer surgery is incomplete resection, or the presence of microscopic tumor cells at the resection margin. The likelihood of such an occurrence is reduced but not eliminated by the use of frozen section histology, which has a greatly reduced accuracy without the facility of immunohistochemistry to identify tumor cells. Secondly, many cancers infiltrate along lymphatic channels or follow perineural lymphatics where they are impossible to detect at the time of surgery.

Tumor cells can be left behind during cancer surgery because they have invaded into a critical structure that cannot be safely resected or reconstructed in an individual patient. In many cases, the index operation is such a physical and metabolic insult to the patient's physiology that re-operation and further resection is just not possible. In these cases, survival of the individual patient with positive margins is greatly and significantly reduced from an equivalent patient with clear margins.

The current process to manage close or positive margins is chemotherapy with or without adjuvant radiotherapy to the operative bed. This treatment is often ineffective at preventing local recurrence, and highly toxic. The doses of radiation achieved by the tumor cells are severely limited because of the presence of radiosensitive surrounding structures like the bowel, and the need to wait for reconstructed structures (like anastomoses) to heal before the commencement of chemotherapy.

This results in an ineffective radiation dose to the operative bed for tumor control, and a delay often up to 8-10 weeks before chemotherapy is instituted. In this time, the immunological/inflammatory insult of major surgery decreases the body's ability to fight tumor cells, and the cells at positive margin are left untreated, which results often in local cancer recurrence, which can then metastasize throughout the body.

Recently the utility for high dose rate brachytherapy devices for managing inoperable tumors has increasingly been recognized. Devices devised from beta radio-active particles injected intra-arterially have shown potential in managing inoperable liver tumors, and a beta-emitter suspended in a silica diluent has shown early clinical potential for injection or positioning directly into inoperable pancreatic tumors through special applicators inserted into body cavities or tissues. Barriers to creation of such a routine surgical device include high cost, moderate inflexibility, radioactive seed migration and non-target radiation, non-bioresorbable radio-isotope sources, a lack of absorbable unidirectionality, and containment of the radio-isotope.

There is a need for an improved therapeutic patch to treat residual tumor cells that remain in a patient at a wound location once the tumor has been surgically removed.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

BRIEF SUMMARY

In at least one aspect there is provided a flexible bioresorbable brachytherapy device for application on a wound site in a subject, the device comprising:

a sealed radioactive source having opposite first and second sides, wherein the sealed radioactive source comprises:

a radioactive component comprising a plurality of radio-isotope particles dispersed within a carrier, a barrier surrounding the radioactive component providing the sealed radioactive source, wherein the barrier functions as a barrier, when implanted at the wound site, providing the sealed radioactive source for at least six half-lives of the plurality of radio-isotope particles, a bioresorbable shield located on the first side of the sealed radioactive source, the bioresorbable shield configured to shield radioactivity when implanted at the wound site for at least six half-lives of the plurality of radio-isotope particles.

In another aspect there is provided a method of preparing a flexible bioresorbable brachytherapy device described herein.

In yet another aspect there is provided a method of treating a tumor, the method comprising applying into an anatomic area affected by the tumor a device described herein.

In another aspect there is provided a method for minimizing and/or controlling uncontrolled growth of tumor cells at margins of a wound site in a subject following surgery, the method comprising applying the device to the wound site.

In another aspect there is provided a method of reducing tumor load in an individual, the method comprising applying into an anatomic area affected by the tumor a device described herein.

In another aspect there is provided a method of reducing the severity, or minimizing the progression, of a tumor in an individual, the method comprising applying into an anatomic area affected by the tumor a device described herein.

In another aspect there is provided a method for minimizing and/or controlling local recurrence of tumor cells at margins of a wound site in a subject, the method comprising applying the device to the wound site. In at least one embodiment, the method comprises minimizing and/or controlling local recurrence of malignant cancer and seroma at margins of a wound site in a subject following cancer surgery.

Further aspects of the present disclosure and further embodiments of the aspects described in the preceding paragraphs will become apparent from the following description, given by way of example and with reference to the accompanying drawings.

DETAILED DESCRIPTION

Figure 1:
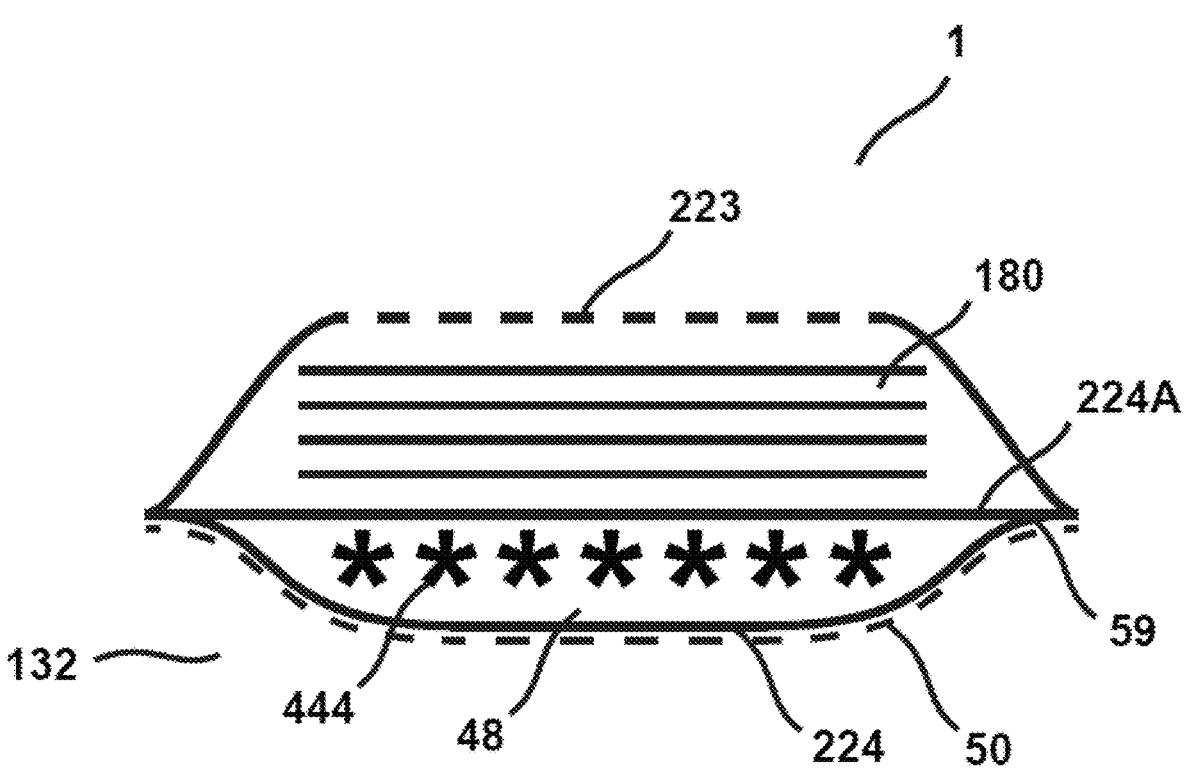
FIG. 1 is a cross-sectional view of a flexible bioresorbable brachytherapy device according to a preferred embodiment of the present disclosure.

It will be understood that the disclosure in this specification extends to all alternative combinations of two or more of the individual features mentioned or evident from the text or drawings. All of these different combinations constitute various alternative aspects of the disclosure.

Reference will now be made in detail to certain embodiments of the disclosure. While the disclosure will be described in conjunction with the embodiments, it will be understood that the intention is not to limit the disclosure to those embodiments. On the contrary, the disclosure is intended to cover all alternatives, modifications, and equivalents, which may be included within the scope of the present disclosure.

One skilled in the art will recognize many methods and materials similar or equivalent to those described herein, which could be used in the practice of the present disclosure. The present disclosure is in no way limited to the methods and materials described. It will be understood that the disclosure disclosed and defined in this specification extends to all alternative combinations of two or more of the individual features mentioned or evident from the text or drawings. All of these different combinations constitute various alternative aspects of the disclosure.

All of the patents and publications referred to herein are incorporated by reference in their entirety.

Definitions

For the purposes of interpreting this specification, terms used in the singular will also include the plural and vice versa. For example, "a" means one or more unless indicated otherwise.

As used herein, except where the context requires otherwise, the term "comprise" and variations of the term, such as "comprising," "comprises" and "comprised," are not intended to exclude further additives, components, integers or steps.

The use of the term "about" includes and describes the value or parameter per se. For example, "about x" includes and describes "x" per se. In some embodiments, the term "about" when used in association with a measurement, or used to modify a value, a unit, a constant, or a range of values, is meant to encompass variations of ±20% or ±10%, in some instances ±5%, in some instances ±1%, and in some instances ±0.1% from the specified value, as such variations are appropriate in various aspects of the disclosure. For example, "about 400" in some embodiments includes 360-440.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6. This applies regardless of the breadth of the range.

It will be understood that when an element is referred to as being "on," "attached" to, "connected" to, "coupled" with, "contacting," etc., another element, it can be directly on, attached to, connected to, coupled with, or contacting the other element or intervening elements may also be present. In contrast, when an element is referred to as being, for example, "directly on," "directly attached" to, "directly connected" to, "directly coupled" with, "directly contacting," etc., another element, there are no intervening elements present. It will also be appreciated by those skilled in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element, component, region, layer or section discussed below could also be termed a "second" element, component, region, layer or section without departing from the teachings of the present disclosure. The terms "first side" and "second side" as used in the statements of disclosure indicate frames of reference, rather than physical features, i.e., being arranged on a first side or a second opposite side of the sealed radioactive source. The sequence of operations (or steps) is not limited to the order presented in the claims or figures unless specifically indicated otherwise.

As used herein, the term "contacting" is meant to broadly refer to bringing a cell or tissue and a device of the present disclosure into sufficient proximity that the device can exert an effect on the cell or tissue. The skilled artisan will understand that the term "contacting" includes physical interaction between a device and a cell or tissue.

Herein, the terms "individual," "subject" or "patient" can be used interchangeably with each other. The terms "individual," "subject" or "patient" refer to an animal that is treatable by the device and/or method, respectively, including but not limited to, for example, dogs, cats, horses, sheep, pigs, cows, and the like, as well as human, non-human primates. Unless otherwise specified, the "individual," "subject" or "patient" may include both male and female genders. Further, it also includes a subject, preferably a human, suitable for receiving treatment with a device and/or method of the present disclosure.

The terms "treat," "treatment" or "treating" of a subject includes delaying, slowing, stabilizing, curing, healing, alleviating, relieving, altering, remedying, less worsening, ameliorating, improving, or affecting the disease or condition, the sign or symptom of the disease or condition, or the risk of (or susceptibility to) the disease or condition. The disease or condition herein generally refers to cancer. The term "treating" refers to any indication of success in the treatment or amelioration of an injury, pathology or condition, including any objective or subjective parameter such as abatement; remission; lessening of the rate of worsening; lessening severity of the disease; stabilization, diminishing of signs or symptoms or making the injury, pathology or condition more tolerable to the individual; slowing in the rate of degeneration or decline; making the final point of degeneration less debilitating.

"Neoplasia" generally refers to uncontrolled, abnormal growth of cells or tissues in a subject.

A "neoplasm" or "tumor" generally refers to an abnormal mass of tissue in a subject. A "neoplasm" and "tumor" may be classified as benign (noncancerous), pre-cancerous, pre-neoplastic or malignant (cancerous).

"Pre-cancerous" or "pre-neoplasia" generally refers to a condition or a growth that typically precedes or develops into a cancer. A "pre-cancerous" growth may have cells that are characterized by abnormal cell cycle regulation, proliferation, or differentiation, which can be determined by markers of cell cycle.

"Cancer" generally refers to a disease or condition caused by an uncontrolled division of abnormal cells that have become malignant.

"A condition or symptom associated" with neoplasia may be any pathology that arises as a consequence of, preceding, or proceeding from the neoplasm.

In some embodiments, the methods of the present disclosure can be to prevent or reduce the severity, or inhibit or minimize progression, of a sign or symptom of a disease or condition as described herein. As such, the methods of the present disclosure have utility as treatments as well as prophylaxis.

As used herein, the terms "inhibit," "inhibiting" and "inhibition" have their ordinary and customary meanings, and includes inhibiting local recurrence of tumor cells. Such inhibition is an inhibition of about 1% to about 100% of the particular activity versus the activity in a subject to which a device of the present disclosure has not been administered. Preferably, the inhibition is an inhibition of 100%, 99%, 98%, 97%, 96%, 95%, 90%, 80%, 70%, 60%, 50%, 40%, 30%, 20%, 10%, 5% or 1% of the activity versus a subject to which a device of the present disclosure has not been administered.

"Regression" and "regress" and "regresses" generally refers to the reduction in tumor cells or tissue, reduction in growth of tumor cells or tissue, resulting in the complete or partial involution or elimination of tumor cells or tissue.

A "complete response" to therapy is generally understood as meaning the disappearance of all detectable signs of neoplasia in response to treatment. According to the disclosure, a complete response arises from the elimination of tumor cells or tissue by irradiation. A complete response may include a "radiological complete response" wherein there are no observable signs of neoplasia as determined from an imaging scan, or a "biochemical complete response" wherein blood markers associated with the neoplasia return to normal levels.

A "partial response" is generally understood as meaning a decrease in tumor load in an individual, for example in terms of number of tumor cells and growth rate. A partial response may increase the time to disease progression and/or disease recurrence. According to the disclosure, a partial response may arise from the regression of tumor cells or tissue by irradiation.

As used herein, the term "radionuclide" (also commonly referred to as a radio-isotope or radioactive isotope) is an atom with an unstable nucleus. It radioactively decays resulting in the emission of nuclear radiation (such as gamma rays and/or subatomic particles such as alpha or beta particles).

As used herein, the term "biocompatible" refers to components that are neither themselves toxic to the subject (e.g., an animal or human) nor degrade at a rate that produces monomeric or oligomeric subunits or other byproducts at toxic concentrations to the subject.

As used herein, the term "biodegradable" refers to components that are intended to degrade during in vivo use, such as implantation. In general, degradation attributable to bio-degradability involves degradation of, for example, a bio-degradable polymer into its component subunits, or diges-tion, e.g., by biochemical process carried out for example by enzymes, of the polymer into smaller non-polymeric sub-units.

As used herein, the term "hydrogel" refers to a biphasic material comprising a mixture of porous, permeable solids and at least 10% by weight or volume of interstitial fluid composed of an aqueous solution, typically water, buffer or biological fluids. Hydrogels are typically formed by cross-linking water soluble molecules to form networks of essen-tially infinite molecular weight. Hydrogels with high water contents are typically soft, pliable materials. A hydrogel that has been dried is referred to herein as a dehydrated hydrogel if it is capable of returning to a hydrogel state upon exposure to water; this hydrogel would expand in volume if it were exposed to an excess of water and not constrained. The term desiccated refers to a hydrogel essentially having no fluids, bearing in mind that some trace amounts of water may nonetheless be present. The term "hydrogel" as used herein refers to a dehydrated hydrogel, desiccated hydrogel and hydrated hydrogel unless indicated otherwise.

As used herein, the term "equilibrium water content" refers to the amount of water (or aqueous solution) in a hydrated hydrogel by weight.

Brachytherapy Device

In at least one aspect there is provided a flexible biore-sorbable brachytherapy device for application on a wound site in a subject, the device comprising:
- a sealed radioactive source having opposite first and second sides, wherein the sealed radioactive source comprises:
- a radioactive component comprising a plurality of radio-isotope particles dispersed within a carrier,
- a barrier surrounding the radioactive component provid-ing the sealed radioactive source,
- wherein the barrier functions as a barrier, when implanted at the wound site, providing the sealed radioactive source for at least six half-lives of the plurality of radio-isotope particles,
- a bioresorbable shield located on the first side of the sealed radioactive source, the bioresorbable shield con-figured to shield radioactivity when implanted at the wound site for at least six half-lives of the plurality of radio-isotope particles.

The device may be sutured, stapled or adhered to the wound site.

In a preferred embodiment, the device comprises an adhesive layer located on the second side of the sealed radioactive source, wherein the adhesive layer is applied to the wound site. In a most preferred embodiment, the adhe-sive layer is a hydrophilic adhesive layer that adheres to the wound site.

In a preferred embodiment, the device is in the form of a layered structure. Such layers may include any one or more of the following: the carrier for the radio-isotope particles; one or more layer(s) defining the barrier; the bioresorbable shield; and optionally the adhesive layer. Each of these layers may be comprised of one or more sub-layers. For example, the bioresorbable shield may be comprised of a plurality of sheets. The barrier may be comprised of a first layer on the first side of the sealed radioactive source and a second layer on the second side of the sealed radioactive source. Each of the layers is suitably flexible. Each of the layers is suitably bioresorbable. While various layers are described herein, this does not preclude the existence of additional and/or intervening layers. The described arrange-ment of the layers does not preclude the existence of additional intervening layers, unless the description indi-cates that one particular layer is directly adjacent to another layer.

The device is entirely or substantially bioresorbable within the subject. Preferably, the device is at least about 90% to 100% bioresorbable, including at least about 90%, 91%, 92%, 93%, 94%, 95%, 96%, 97%, 98%, 99%, and 100% bioresorbable.

The device may be configured with material(s) degradable by hydrolysis.

It is an advantage that the plurality of radio-isotope particles are provided in a sealed source and thereby main-tained physically in place within the sealed source at the wound site until the time they are no longer capable of delivering a clinically significant dose of radiation. More particularly, relative movement of the plurality of radio-isotope particles within the sealed source is minimized. It is a further advantage that the device is configured to be bioresorbable in the subject. In this way, the device may be degraded in vivo. It is a further advantage that the device is configured to be flexible and conform to the wound site.

Radio-Isotope

The radio-isotope particles may comprise an alpha-emitter, a beta-emitter, a gamma-emitter, or combinations thereof. In a preferred embodiment, the radio-isotope particles comprise a beta-emitter. The radio-isotope particles may comprise one or more of: Yttrium-90, Iridium-192, Chromium-51, Palladium-103, Caesium-131, Iodine-131, Iodine-125, Iodine-123, Samarium-153, Lutetium-177, 33-Phosphorus (33P), 32-Phosphorus (32P), and compounds containing such isotopes. In a preferred embodiment, the radio-isotope particles may comprise one or more of: Yttrium-90, Iridium-192, Palladium-103, Caesium-137, Iodine-131, Samarium-153, Lutetium-177, 33-Phosphorus (33P), 32-Phosphorus (32P), and compounds containing such isotopes. In a particularly preferred embodiment, the radio-isotope particles may comprise: 33-Phosphorus (33P), 32-Phosphorus (32P), compounds containing such isotopes, and combinations thereof. It is to be appreciated that in this description, radio-isotope particles can include compounds that contain radio-isotopes.

In a preferred embodiment, the radio-isotope particles are insoluble radio-isotope particles.

In at least one embodiment, the plurality of radio-isotope particles may comprise radioactive elements in the compound molecules of calcium phosphate. The compound molecules of calcium phosphate may comprise one or more of: calcium pyrophosphate, monocalcium phosphate, dicalcium phosphate, octacalcium phosphate, tricalcium phosphate, hydroxyapatite, fluoroapatite, tetracalcium phosphate and other trace elements.

Carrier

In a preferred embodiment, the carrier is hydrophilic. More preferably the carrier comprises a biocompatible, biodegradable hydrophilic polymer.

In some embodiments, the biocompatible, biodegradable hydrophilic polymer may be capable of being crosslinked into a bioresorbable hydrogel. Preferably, the biocompatible, biodegradable hydrophilic polymer is crosslinked to completion. Crosslinked to completion means that there are substantially no unpolymerized functional groups available for crosslinking for example by radiation emitted from the radio-isotopes in the device or during gamma sterilization processing. Polymerizable functional groups of the polymer(s) that are not crosslinked in the biocompatible, biodegradable hydrophilic polymer are herein referred to as unpolymerized functional groups. Preferably, unpolymerized functional groups are reacted during crosslinking to form bonds to minimize further crosslinking, for example by radiation emitted from the radio-isotopes in the device or during gamma sterilization processing. Unpolymerized functional groups may be reacted to form nonreactive groups by any method known to those skilled in the art including, but not limited to: heat, and/or hydrolysis.

In a preferred embodiment, the carrier comprises a biocompatible, biodegradable insoluble hydrophilic polymer. A skilled person will understand that any suitable biocompatible, biodegradable insoluble hydrophilic polymer may be used. The biocompatible, biodegradable insoluble hydrophilic polymer may or may not be crosslinked, preferably not crosslinked. Suitable polymers include, but are not limited to: polyvinyl alcohol (herein abbreviated as PVOH), cellulose, carboxymethyl cellulose, starch, alginate, polyglycerol sebacate, polyethylene-co-vinyl acetate, polyethylene glycol, polyvinylpyrrolidone, gelatin, chitosan, dextran, derivatives thereof, and combinations thereof.

In a particularly preferred embodiment, the carrier comprises PVOH. Preferably, the PVOH polymer has a molecular weight of about 60 to about 200 kDa, including about 60, 124, 145 and 200 kDa. Preferably, the PVOH has a degree of hydrolysis of about 80% to about 99%, including about 80%, 81%, 82%, 83%, 84%, 85%, 86%, 87%, 88%, 89%, 90%, 91%, 92%, 93%, 94%, 95%, 96%, 97%, 98% and 99%, most preferably about 88%. Preferably, the carrier comprises a dried film of insoluble PVOH, wherein the PVOH is insoluble under physiological conditions.

Preferably the radio-isotope particles are substantially uniformly dispersed or distributed within the carrier.

Sealed Source

The radioactive component, comprising the plurality of radio-isotope particles dispersed within the carrier, is surrounded by a barrier to provide a sealed radioactive source. The barrier inhibits leaching of radio-isotope particles from the sealed source, for example, to other components in the device and/or surrounding tissue. The barrier may substantially inhibit movement, transfer, dispersion or leaching of components between the sealed source and the surrounding environment, for example dispersion of components within the sealed source to outside the sealed source. The barrier physically maintains the plurality of radio-isotope particles within the sealed source. Preferably, the barrier also substantially inhibits movement, transfer or dispersion of components outside the sealed source to within the sealed source.

In a preferred embodiment, the barrier comprises a biocompatible, biodegradable hydrophobic polymer. Suitable polymers include, but are not limited to: polycaprolactone (PCL), polylactide (PLA), poly(L-lactic acid) (PLLA), poly (D-lactic acid) (PDLA), poly(lactic-co-glycolic acid) (PLGA), polydioxanone, caprolactone, glycolic acid, lactic acid, lactate-co-glycolate, polyurethane, and combinations thereof.

In at least one embodiment, the barrier may comprise layers that are joined. For example, the barrier may be in the form of a pouch or envelope. The barrier may comprise a first layer arranged on the first side of the sealed radioactive source and a second layer arranged on the second side of the sealed radioactive source, wherein the first and second layers are sealed to surround the radioactive component. The layers may be discrete sheets which overlap and are sealed to surround the radioactive component. Alternatively, the first and second layers may be defined by a single folded sheet which has two parts defining respective ones of the first and second layers which overlap and are sealed to surround the radioactive component. The first and second layers may be sealed at the peripheral edges or adjacent to the peripheral edges. In a most preferred form, the pouch or envelope may comprise opposite upper and lower layers that are sealed around an external periphery thereby surrounding and encapsulating the radioactive component. In this embodiment, the upper layer corresponds to the first layer and the lower layer corresponds to the second layer.

The composition of the first and second layers of the barrier may be the same or different, preferably the same.

In a preferred embodiment, the barrier may be in the form of a continuous structure surrounding the radioactive component.

In a preferred embodiment, the barrier comprises PCL, preferably about 80-99.9% w/v PCL. Preferably, the PCL comprises a molecular weight of about 70 to about 200 kDa, including any range or value therein including, but not limited to, about 70 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa.

Preferably, the PCL comprises a molecular weight of about 77 kDa to about 150 kDa. The PCL may be amorphous or crystalline.

In at least one embodiment, the barrier inhibits leaching of radio-isotope particles between the sealed source and the surrounding environment by at least about 95% to about 100%, including any range or value therein, including at least about 95%, 96%, 97%, 98%, 99%, or 100%. Most preferably, the barrier inhibits leaching of radio-isotope particles between the sealed source and the surrounding environment by at least about 99%, 99.1%, 99.2%, 99.3%, 99.4%, 99.5%, 99.6%, 99.7%, 99.8%, 99.9% or 100%, most preferably by at least about 99.9%.

In at least one embodiment, the barrier inhibits leaching of radio-isotope particles from the sealed source to the surrounding environment such that the amount of radioactivity leached into the surrounding environment is less than about 200 Bq per day, preferably less than about 100 Bq.

In another embodiment, the barrier inhibits leaching of radio-isotope particles from the sealed source to the surrounding environment such that the amount of radioactivity leached into the surrounding environment is no more than about 200 B q per day preferably no more than about 100 Bq, most preferably no more than about 200 B q per day.

In another embodiment, the barrier inhibits leaching of radio-isotope particles from the sealed source to the surrounding environment such that the amount of radioactivity leached into the surrounding environment is about 200 B q per day, preferably about 100 Bq, most preferably about 200 B q per day.

Preferably, the radioactive source is fully sealed. A fully sealed radioactive source completely inhibits leaching of radio-isotope particles from the sealed source, for example to surrounding tissue, and thereby inhibits leaching by about 100%. The device has the advantage of being a sealed source while significantly radioactive.

Preferably, the plurality of radio-isotope particles are physically maintained in place within the sealed source such that relative movement of the plurality of radio-isotope particles is minimized. Relative movement of the plurality of radio-isotope particles refers to movement of one radio-isotope particle relative to another radio-isotope particle. More particularly, movement of a first radio-isotope particle of the plurality of radio-isotope particles relative to a second radio-isotope particle of the plurality of radio-isotope particles. A skilled person will understand that relative movement does not include movement due to the inherent flexibility of the device, but refers to movement greater than the inherent flexibility of the device. In such embodiments, the relative location of the plurality of radio-isotope particles within the sealed source is substantially maintained.

In at least one embodiment, the plurality of radio-isotope particles are physically maintained in place within the sealed source, when implanted at the wound site, such that relative movement of the plurality of radio-isotope particles is minimized for at least six half-lives of the plurality of radio-isotope particles. Preferably, the relative movement of the plurality of radio-isotope particles is minimized for at least about 6 to 10 half-lives of the plurality of radio-isotope particles, including at least about 6 half-lives, 7 half-lives, 8 half-lives, 9 half-lives, and 10 half-lives, most preferably at least about 10 half-lives. In this way, the relative location of the plurality of radio-isotope particles within the sealed source is maintained for at least six half-lives of the plurality of radio-isotope particles.

Preferably, the sealed radioactive source is in the form of a unified structure, which may be comprised of one or more parts, wherein the structure does not separate into multiple parts in use. In this way the sealed radioactive source in the form of a unified structure enables the relative location of the plurality of radio-isotope particles within the sealed source to be substantially maintained.

In at least one embodiment, the sealed radioactive source may comprise a continuous radiation pattern. For example, the sealed radioactive source may comprise a single continuous radioactive component surrounded by a single barrier. The single continuous radioactive component may be in the form of a single planar structure. The barrier may surround the single planar structure.

In another embodiment, the sealed radioactive source may comprise a discontinuous radiation pattern. For example, the sealed radioactive source may comprise two or more discrete, spatially separated radioactive components such that the sealed radioactive source includes one or more regions that are substantially free of radioactive material. An example of such an embodiment includes radioactive components in the form of spaced apart dots. The spatially separated radioactive components may be surrounded by a single barrier providing a unified radiation source. Alternatively the upper and lower layers of the barrier may be joined at additional locations to provide two or more sealed pouches, or pockets within the unified sealed radioactive source. In such embodiments, the spatially separated radioactive components may each be surrounded by a barrier such that the sealed radioactive source comprises two or more discrete, spatially separated radioactive components, each surrounded by a barrier. The two or more discrete, spatially separated radioactive components remain in a substantially fixed location relative to one another within the unified sealed radioactive source. In this way, the relative location of the plurality of radio-isotope particles within the sealed source is substantially maintained.

An advantage of a unified, sealed radioactive source is that when implanted at the wound site, relative movement of the plurality of radio-isotope particles is minimized thereby providing a consistent radiation dose to the wound site. Preferably, the radioactive component is uniformly dispersed or distributed throughout the sealed source, thereby providing a consistent, uniform radiation dose to the wound site.

In a preferred embodiment, wherein the radio-isotope particles comprise an alpha emitter or a beta emitter, and the sealed radioactive source is configured to deliver substantially no radiation at a depth of about 8 to 9 mm, including about 8.0 mm, 8.1 mm, 8.2 mm, 8.3 mm, 8.4 mm, 8.5 mm, 8.6 mm, 8.7 mm, 8.8 mm, 8.9 mm, and 9.0 mm. Substantially no radiation refers to less than about 10 Gray, preferably less than about 5 Gray.

It is an advantage of the device that the plurality of radio-isotope particles are maintained in place within the sealed radioactive source until the time they are no longer capable of delivering a clinically significant dose of radiation. Herein radio-isotope particles are considered no longer capable of delivering a clinically significant dose of radiation after at least about 6 half-lives of the plurality of radio-isotope particles, including at least about 6 half-lives, 7 half-lives, 8 half-lives, 9 half-lives, and 10 half-lives, preferably at least about 10 half-lives. Radio-isotope particles may also be considered no longer capable of delivering a clinically significant dose of radiation when the radioactivity of the radio-isotope particles comprises no more than about 1.6% of the radioactivity of the original radio-isotope particles, no more than about 0.8%, no more than about 0.4%, no more than about 0.2%, no more than about 0.1%, preferably no more than about 0.1%.

In at least one embodiment, the barrier functions as a barrier, when implanted at the wound site, providing the sealed source for at least six half-lives of the plurality of radio-isotope particles. Preferably, the barrier functions as a barrier for at least about 6 to 10 half-lives of the plurality of radio-isotope particles, including at least about 6 half-lives, 7 half-lives, 8 half-lives, 9 half-lives, and 10 half-lives, most preferably at least about 10 half-lives. In this way, the plurality of radio-isotope particles is localized to the barrier for at least six half-lives of the plurality of radio-isotope particles.

In o at least ne embodiment, the barrier persists for at least six half-lives of the plurality of radio-isotope particles.

In another embodiment, the barrier remains substantially undegraded for at least six half-lives of the plurality of radio-isotope particles.

In at least one embodiment, the barrier is configured to degrade, when implanted at the wound site, at a rate whereby the barrier remains substantially undegraded for at least six half-lives of the plurality of radio-isotope particles such that the plurality of radio-isotope particles is localized to the barrier for at least six half-lives of the plurality of radio-isotope particles. For instance, the degradation of the barrier may be such that egress of components from the sealed source to the surrounding environment is at least substantially precluded (or in an ideal embodiment, fully prevented) until at least six half-lives of the plurality of radio-isotope particles has elapsed. Preferably, the barrier is configured to degrade at a rate whereby the barrier remains substantially undegraded for at least about 6 to 10 half-lives of the plurality of radio-isotope particles, including at least about 6 half-lives, 7 half-lives, 8 half-lives, 9 half-lives, and 10 half-lives.

In at least one embodiment, the sealed radioactive source is configured to act as a sealed radioactive source, when implanted at the wound site, for at least six half-lives of the plurality of radio-isotope particles. Preferably, the sealed radioactive source is configured to act as a sealed radioactive source for at least about 6 to 10 half-lives of the plurality of radio-isotope particles, including at least about 6 half-lives, 7 half-lives, 8 half-lives, 9 half-lives, and 10 half-lives, most preferably at least about 10 half-lives. In this way, the plurality of radio-isotope particles is localized to the sealed radioactive source for at least six half-lives of the plurality of radio-isotope particles.

In at least one embodiment, the sealed radioactive source persists for at least six half-lives of the plurality of radio-isotope particles.

In another embodiment, the sealed radioactive source remains substantially undegraded for at least six half-lives of the plurality of radio-isotope particles.

In at least one embodiment, the sealed radioactive source is configured to degrade, when implanted at the wound site, at a rate whereby the sealed radioactive source remains substantially undegraded for at least six half-lives of the plurality of radio-isotope particles such that the plurality of radio-isotope particles is localized to the barrier for at least six half-lives of the plurality of radio-isotope particles. Preferably, the sealed radioactive source is configured to degrade at a rate whereby the sealed radioactive source remains substantially undegraded for at least about 6 to 10 half-lives of the plurality of radio-isotope particles, including about 6 half-lives, 7 half-lives, 8 half-lives, 9 half-lives, and 10 half-lives, most preferably at least about 10 half-lives. In this way, the plurality of radio-isotope particles is localized to the sealed radioactive source for at least six half-lives of the plurality of radio-isotope particles.

It will be understood that once the barrier degrades, the radioactive component is no longer sealed and the components, including the particles and carrier therein, as well as the barrier, may disperse throughout the subject and biodegrade. Preferably, the barrier degrades after the radiation has substantially decayed. Preferably, the barrier remains substantially undegraded until at least about 98% radiation has decayed. Preferably, the barrier does not substantially degrade until at least about 98% radiation has decayed. Preferably, the barrier degrades after at least 98% radiation has decayed. Substantially undegraded herein means that the barrier functions as a barrier and is configured to substantially inhibit leaching of radio-isotope particles as defined herein. Substantially undegraded may refer to any amount of barrier remaining that inhibits leaching of radio-isotope particles as defined herein.

In a preferred embodiment, the second side of the radioactive source is functionalized to provide a hydrophilic surface. For example, the second side of the radioactive source may comprise a biocompatible, biodegradable hydrophobic polymer functionalized to provide a hydrophilic surface. The surface may be functionalized by any chemical or physical means known to those skilled in the art, including but not limited to: plasma treatment, radiation, UV crosslinking, or chemical modification such as arginine functionalization. Preferably the first and second layers of the barrier are arranged respectively, on the first and second sides of the sealed radioactive source. Accordingly, the second layer of the barrier may have a lower surface (relative to the configuration of the sealed radioactive source) which is functionalized to provide a hydrophilic surface.

Adhesive Layer

An adhesive layer may be located on the second side of the radioactive source. In such embodiments, the adhesive layer forms the bottommost layer of the device. The adhesive layer may be applied to the wound site.

In at least one embodiment, the adhesive layer is a hydrophobic pressure sensitive adhesive layer that is adapted to adhere to the wound site.

In another embodiment, the adhesive layer is a hydrophilic adhesive layer that is adapted to adhere to the wound site.

Preferably, the second side of the radioactive source and the adhesive layer are directly contacted. In a preferred embodiment, the adhesive layer is directly adjacent to the lower surface of the second layer of the barrier.

In a preferred embodiment, the functionalized surface of the second side of the radioactive source and the hydrophilic adhesive layer are directly contacted, more preferably, covalently bonded to one another. In a preferred embodiment, the hydrophilic layer is directly adjacent to the second layer of the barrier, and most preferably directly adjacent to the functionalized surface of the second layer of the barrier.

The adhesive layer may be in the form of an adhesive coating arranged on functionalized surface of the second side of the radioactive source.

The adhesive layer may be comprised of a crosslinked polymer.

The adhesive layer may comprise other surgical adhesive substances, such as carbodiimide crosslinking, dopa-lysine interactions, or citric acid crosslinking. The adhesive layer may comprise a portion of substances required to create amide bonds and/or hydrogen-hydrogen interactions between the device and tissues of the wound site in the subject. In this way, an additive substance may activate the crosslinking between the device and the tissues, such as 1-Ethyl-3-(3-dimethylaminopropyl) carbodiimide (EDC), dopa, or other crosslinking agent.

In other examples the adhesive layer may comprise a thin layer of bio-compatible resin, gel, or flexible biopolymer such that it absorbs water rapidly to conform with the operative bed. Other polymers derived from cellulose may also be used.

In some examples the hydrophilic adhesive layer comprises one or more of: polysaccharide, glycerol, starch, carboxymethyl cellulose (CM C), xylitol, citric acid, variations thereof, and combinations thereof. Preferably the polysaccharide is pectin. In a particularly preferred embodiment, the hydrophilic adhesive layer comprises: polysaccharide, CM C, carbodiimide crosslinking and combinations thereof. Preferably the polysaccharide is pectin.

The adhesive layer is preferably inert.

In some embodiments, the hydrophilic adhesive layer is supplied in a fully hydrated state, at a similar equilibrium water content to the hydrogel layer. In this way, the fully hydrated hydrophilic adhesive layer may be unlikely to undergo a dramatic change in size and/or modification in shape upon implantation and crosslinking to the tissues of the wound site.

In a preferred embodiment, the hydrophilic adhesive layer is supplied in a dehydrated state and the hydrophilic adhesive layer absorbs moisture from an aqueous solution in use to allow wetting and gelation of the hydrophilic adhesive layer to conform to the wound site. The aqueous solution may be water, saline solution, buffer solution or bodily fluids such as blood, blood product or plasma.

The adhesive layer may also comprise a radio-sensitizing agent, such as gemcitabine or capecitabine. The radio-sensitizing agent may be suspended in the adhesive layer by a solvent casting technique, solution immersion, or melt extrusion technique. In this way, when the wound site absorbs the adhesive layer the radio-sensitizing agent may release. This may have the effect of making tumor cells that are in or close to the wound site susceptible to radiation from the plurality of radio-isotope particles.

The adhesive layer may extend beyond the peripheral edges of the sealed radioactive source. The adhesive layer may be a continuous layer. In some embodiments, the adhesive layer may not be continuous on the second side of the radioactive source. For instance, in some embodiments, the adhesive layer may be distributed in a pattern across the second side of the radioactive source. For example, the adhesive layer may be applied as a matrix of dots of adhesive.

In some examples the adhesive layer provides a concomitant hemostatic effect on the wound site, covalent bonding providing a tamponade effect preventing hematoma which may lift the device away from the wound site. In other examples, the adhesive layer may further comprise a coating or suspension of a hemostatic agent, such as thrombin, fibrin, fibrinogen or other hemostatic agents to augment the hemostatic properties of the adhesive layer.

Bioresorbable Shield

The bioresorbable shield is located on the first side of the radioactive source. The bioresorbable shield is configured to absorb radiation. The bioresorbable shield is configured to absorb at least about 90% to at least about 100% radiation from the sealed radiation source, including any range or value therein, including at least about 90%, 91%, 92%, 93%, 94%, 95%, 96%, 97%, 98%, 99%, or 100% radiation.

Preferably, the bioresorbable shield is in the form of a dehydrated hydrogel layer.

Suitable hydrogels may be formed from natural, synthetic, or biosynthetic polymers. Natural polymers may include glycosaminoglycans, polysaccharides, and proteins. Some examples of glycosaminoglycans include dermatan sulfate, hyaluronic acid, the chondroitin sulfates, chitin, heparin, keratan sulfate, keratosulfate, and derivatives thereof.

Examples of natural polysaccharides include, but are not limited to, carboxymethyl cellulose or oxidized regenerated cellulose, natural gum, agar, agarose, sodium alginate, carrageenan, fucoidan, furcellaran, laminarin, hypnea, eucheuma, gum arabic, gum ghatti, gum karaya, gum tragacanth, locust beam gum, arabinogalactan, pectin, amylopectin, gelatin, hydrophilic colloids such as carboxymethyl cellulose gum or alginate gum cross-linked with a polyol such as propylene glycol, and the like, which form hydrogels upon contact with aqueous surroundings.

Synthetic hydrogels may be biostable or biodegradable. Examples of biostable hydrophilic polymeric materials are polyvinyl alcohol, poly(hydroxyalkyl methacrylate), poly (electrolyte complexes), poly(vinylacetate) cross-linked with hydrolysable or otherwise degradable bonds, and water-swellable N-vinyl lactams. Other hydrogels include hydrophilic hydrogels known as CARBOPOL®, an acidic carboxy polymer (Carbomer resins are high molecular weight, allylpentaerythritol-crosslinked, acrylic acid-based polymers, modified with C10-C30 alkyl acrylates), starch graft copolymers, acrylate polymer, ester cross-linked poly-glucan.

Hydrogels may be made from precursors. The precursors are not hydrogels but are covalently crosslinked with each other to form a hydrogel and are thereby part of the hydrogel. Crosslinks can be formed by covalent or ionic bonds, by hydrophobic association of precursor molecule segments, or by crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form polymers made of repeating units. Precursors may be polymers.

To form covalently crosslinked hydrogels, the precursors must be crosslinked together. In general, polymeric precursors will form polymers that will be joined to other polymeric precursors at two or more points, with each point being a linkage to the same or different polymers. Precursors with at least two reactive groups can serve as crosslinkers since each reactive group can participate in the formation of a different growing polymer chain. In the case of functional groups without a reactive center, among others, crosslinking requires three or more such functional groups on at least one of the precursor types.

The hydrogel layer may be composed of a hydrophilic polymer interpenetrating multi-polymeric hydrogel. This may contain polyvinyl alcohol and carboxymethylcellulose, crosslinked with citric acid. The hydrogel layer may also comprise a blend of copolymer using polyethylene glycol. In some examples a catalyst such as titanium dioxide may be present for the citric acid crosslinking. In yet other examples, other hydrophilic resorbable polymers or sugar alcohols may be used, including but not limited to hydro-lyzed collagen, xanthan gum, sodium alginate, starch, chitosan, forms of cellulose, varieties of collagen, polyethylene glycol, glycerol, sorbitol and the like.

In a preferred embodiment, the hydrogel layer may comprise a biocompatible and biodegradable polymer, preferably an organic polymer. Suitable polymers include, but are not limited to: polyvinyl alcohol (PVOH), carboxymethylcellulose (CM C), polyethylene-co-vinyl acetate, polyethylene glycol, polyvinylpyrrolidone, gelatin, chitosan, dextran, derivatives thereof, and combinations thereof.

In a preferred embodiment, the hydrogel may be in the form of a crosslinked foam. Foams allow for rapid hydration in vivo. The hydrogel foam may be formed by any means known to a person skilled in the art including but not limited to: mechanical means, including whisking, instillation of gas during manufacturing, casting, freeze drying; chemical means using porogens such as sodium bicarbonate, or disintegrins such as croscarmellose; or combinations thereof.

A crosslinking agent may be used to crosslink the biocompatible and biodegradable polymer to form the hydrogel layer. Preferably, the crosslinking agent is citric acid. A percentage of citric acid is selected to specify the rate that the hydrogel layer degrades to maintain structural integrity and shielding capacity. The percentage may be between 2% and 24%, including any range or value therein, including about 2%, 3%, 4%, 5%, 6%, 7%, 8%, 9%, 10%, 11%, 12%, 13%, 14%, 15%, 16%, 17%, 18%, 19%, 20%, 22%, 24%, most preferably about 16%. The citric acid crosslinking may be catalyzed by titanium oxide or augmented by carboxydiimide reactions.

Preferably, the biocompatible and biodegradable polymer (s) of the hydrogel layer is crosslinked to completion.

It will be understood that the thickness of the bioresorbable shield required to shield radioactivity will depend on the type of radio-isotope used in the sealed radiation source. For example, a sealed radiation source comprising a beta emitter, such as a 32P and/or 33P radio-isotope, may require a bioresorbable shield about 5 mm to shield at least about 90% radiation. In a preferred embodiment, the hydrogel layer is about 4 mm, 5 mm, or 6 mm thick. Preferably, the hydrogel layer is at least about 5 mm thick.

It will be appreciated that where the bioresorbable shield is in the form of a hydrogel layer, the hydrogel layer in the device is dehydrated or desiccated, and then in use is hydrated and expands. It will be understood that the hydrogel layer thickness is expressed in terms of equilibrium water content and refers to the thickness of the hydrated hydrogel.

The hydrogel layer may be in the form of a bulk hydrogel. Alternatively, the hydrogel layer may be in the form of a stack comprising two or more strips, sheets or layers to provide the desired hydrogel layer thickness. Preferably, the hydrogel layer is flexible and porous.

The hydrogel layer is configured to absorb aqueous solution. The hydrogel layer expands upon contact with aqueous solution. Preferably the hydrogel layer of the device is provided in the form of a dehydrated or desiccated hydrogel layer. Upon application to a wound site, the hydrogel layer may be contacted with aqueous solution in situ to provide an expanded hydrated hydrogel layer. The hydrogel layer thickness is expressed in terms of equilibrium water content and refers to the thickness of the hydrated hydrogel. The aqueous solution may be water, saline solution, buffer solution or bodily fluids such as blood, blood product or plasma.

The bioresorbable shield may comprise opposite upper and lower surfaces. The lower surface of the bioresorbable shield may be arranged on the first side of the sealed radioactive source.

The lower surface of the bioresorbable shield may be arranged on the first side of the sealed radioactive source.

Where the first and second layers of the barrier are arranged respectively, on the first and second sides of the sealed radioactive source, the first layer of the barrier may have an upper surface. Accordingly, the lower surface of the bioresorbable shield may be arranged above the upper surface of the first layer of the barrier.

In at least one form of the disclosure, the lower surface of the bioresorbable shield may be arranged directly adjacent to the upper surface of the first layer of the barrier.

In a most preferred form of the disclosure, a further hydrophobic polymer layer may be present between the lower surface of the bioresorbable shield and the upper surface of the first layer of the barrier. The further hydrophobic polymer layer may comprise opposite upper and lower surfaces. Accordingly, the lower surface of the bioresorbable shield may be arranged directly adjacent to the upper surface of the further hydrophobic polymer layer, and the lower surface of the further hydrophobic polymer layer may be arranged directly adjacent to the upper surface of the first layer of the barrier.

The further hydrophobic polymer layer may be a continuous layer. Alternatively, the further hydrophobic polymer layer may be discontinuous. For instance, in some embodiments, the further hydrophobic polymer layer may be distributed in a pattern across the lower surface of the bioresorbable shield. For example, the further hydrophobic polymer layer may be applied as a matrix, or a discontinuous net.

Preferably, the further hydrophobic polymer layer comprises PCL, more preferably about 90 to 100% w/v PCL, most preferably pure PCL. Preferably, the PCL polymer comprises a molecular weight of about 80 to about 200 kDa. The PCL may be amorphous or crystalline.

A fenestrated hydrophobic polymer layer may be arranged above the upper surface of the hydrogel layer. Preferably, the fenestrated hydrophobic polymer layer forms the uppermost layer of the device. The fenestrated hydrophobic polymer layer allows aqueous solution to penetrate the hydrogel layer and expand.

In a preferred embodiment, the hydrogel layer comprises PVOH and CM C crosslinked using citric acid. The hydrogel layer may comprise about 2 to 40% w/v PV OH, about 44 to 96% w/v CM C, and about 2 to 24% w/v citric acid. Preferably, the PVOH polymer comprises a molecular weight of about 60 to about 200 kDa, including about 60, 124, 145 and 200 kDa. Preferably, the PVOH is provided in an amount of about 2 to 40% w/v, including any range or value therein, including about 5%, 10%, 15%, 20%, 25%, 30%, 35% and 40%, most preferably about 20%. The PVOH may comprise a degree of hydrolysis of about 8% to about 20%, including about 8%, 9%, 10%, 11%, 12%, 13%, 14%, 15%, 16%, 17%, 18%, 19%, 20%, most preferably about 12%. Preferably, the CM C polymer comprises a molecular weight of about 500 to 900 kDa, including about 500 kDa, 600 kDa, 700 kDa, 800 kDa, 900 kDa, preferably about 700 kDa. Preferably, the CM C is provided in an amount of about 44 to 96% w/v, including any range or value therein, including about 44%, 50%, 60%, 70%, 80%, 90%, 96%, most preferably about 64%. Preferably, the citric acid is provided in an amount of about 2 to 24% w/v, including any range or value therein, including about 2%, 4%, 6%, 7%, 8%, 9%, 10%, 11%, 12%, 13%, 14%, 15%, 16%, 17%, 18%, 19%, 20%, 22%, 24% most preferably about 16%.

In a preferred embodiment, the fenestrated hydrophobic polymer layer comprises PCL, more preferably about 90 to 100% w/v PCL, most preferably pure PCL. Preferably, the PCL polymer comprises a molecular weight of about 80 to about 200 kDa. The PCL may be amorphous or crystalline.

Fenestrations are selected to provide hydration of the hydrogel layer within about 15 seconds to about 5 minutes after contact with an aqueous solution to a thickness that provides a minimum shielding capacity. Minimum shielding capacity refers to a hydrated hydrogel thickness that is capable of absorbing at least about 90% radiation from the sealed radiation source. Preferably, fenestrations are selected to provide hydration of the hydrogel layer within about 15 seconds to about 5 minutes after contact with an aqueous solution to equilibrium water content thickness. Fenestrations may be in the form of pores. Preferably the pores are about 2 to 5 mm in size, including about 2 mm, 3 mm 4, mm and 5 mm. Preferably, the pores have a minimum size of about 2 to 3 mm. Preferably, the pores have a maximum size of about 5 mm.

In a preferred embodiment, the further hydrophobic polymer layer and the fenestrated hydrophobic polymer layer surround the hydrogel layer to form a shielding assembly. The further hydrophobic polymer layer and the fenestrated hydrophobic polymer layer physically maintain the hydrogel layer within the shielding assembly. The fenestrated hydrophobic polymer layer allows movement, transfer or dispersion of components, preferably aqueous solution, outside the shielding assembly to within the shielding assembly. In this way, upon application to a wound site, aqueous solution may penetrate the fenestrated hydrophobic polymer layer thereby contacting the hydrogel layer within the shielding assembly such that the hydrogel layer may hydrate and expand. As described above, the further hydrophobic polymer layer may be a continuous or discontinuous layer. A skilled person will understand that any discontinuous layer configuration capable of physically maintaining the hydrogel layer within the shielding assembly may be suitable. The further hydrophobic polymer layer facilitates manufacture of the device, such that a shielding assembly may be prepared separately to the sealed source. In use, the bioresorbable shield faces away from the wound site.

The bioresorbable shield is configured to shield radioactivity when implanted at the wound site for at least six half-lives of the plurality of radio-isotope particles. Preferably, the bioresorbable shield is configured to shield radioactivity for at least about 6 to 10 half-lives of the plurality of radio-isotope particles, including at least about 6 half-lives, 7 half-lives, 8 half-lives, 9 half-lives, and 10 half-lives, most preferably at least about 10 half-lives. For instance, the degradation of the bioresorbable shield may be such that radiation from the sealed source to the surrounding environment is at least substantially precluded (or in an ideal embodiment, fully prevented) until at least six half-lives of the plurality of radio-isotope particles has elapsed.

In at least one embodiment, the bioresorbable shield persists for at least six half-lives of the plurality of radio-isotope particles.

In another embodiment, the bioresorbable shield remains substantially undegraded for at least six half-lives of the plurality of radio-isotope particles.

The bioresorbable shield is configured to shield radioactivity and to degrade, when implanted at the wound site, at a rate whereby the shielding effect of the bioresorbable shield remains substantially intact for at least six half-lives of the plurality of radio-isotope particles. For instance, the degradation of the bioresorbable shield may be such that radiation from the sealed source to the surrounding environment is at least substantially precluded (or in an ideal embodiment, fully prevented) until at least six half-lives of the plurality of radio-isotope particles has elapsed.

For instance, degradation of the bioresorbable shield may be such that radiation from the sealed source above the uppermost layer of the device is at least substantially precluded (or in an ideal embodiment, fully prevented) until at least six half-lives of the plurality of radio-isotope particles has elapsed.

The bioresorbable shield may also be configured to fully degrade after at least six half-lives of the plurality of radio-isotope particles. In this way, the bioresorbable shield is configured to absorb any emitted radiation to protect surround tissues of the patient and, in some circumstances the operator of the device, such as a surgeon. This is an advantage of the device as the shield provided by the bioresorbable shield assists in the device being unidirectional.

In at least one embodiment, the bioresorbable shield is configured to degrade, when implanted at the wound site, at a rate whereby the bioresorbable shield remains substantially intact for at least six half-lives of the plurality of radio-isotope particles to minimize non-target radiation. Non-target radiation refers to radiation to cells or tissue other than the wound site. Preferably, the bioresorbable shield is configured to degrade, when implanted at the wound site, at a rate whereby the hydrogel layer remains substantially intact for about 6 to 10 half-lives of the plurality of radio-isotope particles, including about 6 half-lives, 7 half-lives, 8 half-lives, 9 half-lives, and 10 half-lives, preferably at least about 10 half-lives. Preferably, the bioresorbable shield degrades after the radiation has substantially decayed. Preferably, the bioresorbable shield remains substantially intact until at least about 98.6% radiation has decayed. Preferably, the bioresorbable shield does not substantially degrade until at least about 98.6% radiation has decayed. Preferably, the bioresorbable shield degrades after at least 98.6% radiation has decayed. Substantially intact may refer to any amount of bioresorbable shield remaining that shields radiation from the sealed radiation source as defined herein.

In at least one embodiment, the bioresorbable shield extends beyond a perimeter of the radioactive component of the sealed radioactive source or in other words, beyond the sealed peripheral containment of the plurality of radio-isotope particles. In such embodiments, the bioresorbable shield, near the perimeter, may be in contact with the adhesive layer. Thus in some examples the sealed radioactive source may be encapsulated by the bioresorbable shield and the adhesive layer.

A contrast agent may be used with the bioresorbable shield, radioactive component, barrier, adhesive layer or combinations thereof. The contrast agent may be a visualization agent that reflects or emits light at a wavelength detectable to a human eye so that a user applying the device may observe the device. In addition, or alternatively, the contrast agent may allow the device to be detected by scanning at a later time, such as with CT, MRI or PET imaging. The contrast agent may be a positive contrast agent, such as gadolinium, bismuth or sulfate, or a negative contrast agent, such as gas bubbles. Preferably, the contrast agent is integrated with the device, such that the relative location of the contrast agent radiological markers is maintained in relation to the plurality of radio-isotope particles for a minimum of 6 half-lives. This enables the location and status of the device to be monitored after it has been implanted in the subject following surgery. Most preferably, the device includes a negative contrast agent in the form of contained gas bubbles within the fenestrated hydrophobic polymer layer.

Methods of Manufacture

Radioactive Component

The radioactive component may be formed by precipitating radioactive ions in the carrier to form a plurality of insoluble radio-isotope particles dispersed within the carrier. The radioactive ions and a precipitant may be mixed in the carrier to form a plurality of insoluble radio-isotope particles dispersed within the carrier.

The radioactive ions may comprise one or more of: Yttrium-90, Iridium-192, Chromium-51, Palladium-103, Caesium-131, Iodine-131, Iodine-125, Iodine-123, Samarium-153, Lutetium-177, 33-phosphorus (33P), 32-phosphorus (32P), and compounds containing such isotopes. In a preferred embodiment, the radio-isotope particles may comprise one or more of: Yttrium-90, Iridium-192, Palladium-103, Caesium-137, Iodine-131, Samarium-153, Lutetium-177, 33-Phosphorus (33P), 32-Phosphorus (32P), and compounds containing such isotopes. In a particularly preferred embodiment, the radio-isotope particles may comprise: 33-Phosphorus (33P), 32-Phosphorus (32P), compounds containing such isotopes, and combinations thereof.

In at least one embodiment, the radioactive ions may be derived from one or more of: monosodium phosphate, disodium phosphate, potassium phosphate, dipotassium phosphate, orthophosphoric acid, tetrasodium pyrophosphate, and soluble compounds containing iodide.

The precipitant may comprise a solution capable of forming any insoluble or poorly soluble salt capable of being bioresorbed in, or excreted from, the subject. These include, but are not limited to, any variety of calcium hydroxide or form of ammonium magnesium phosphate (Struvite). In at least one example, the functional groups of absorbable polymers may be iodinated using radioactive iodide 125 or 131, or crystalline iodide embedded/distributed throughout the carrier substance. In yet other examples the precipitant may comprise another molecule containing calcium, magnesium, zinc or iron.

In at least one example the precipitant comprises an aqueous solution of calcium ions, including the hydroxide, chloride or nitrate forms, or any other alternative aqueous calcium solution. The precipitant may comprise one or more of calcium hydroxide, calcium chloride, calcium nitrate or calcium bromide, or any other alternative aqueous calcium solution. In this way, the plurality of insoluble radio-isotope particles may be elements in the compound calcium pyrophosphate $(Ca_2P_2O_7)$, anhydrous, dihydrate $(Ca_2P_2O_7{\cdot}2H_2O)$ or tetrahydrate $(Ca_2P_2O_7{\cdot}4H_2O)$.

The precipitant may be suspended, dispersed or dissolved in a first solution to form a precipitant solution. Preferably the first solution is an aqueous solution.

The radioactive ions may be suspended, dispersed or dissolved in a second solution to form a radio-isotope solution. Preferably the second solution is an aqueous solution. Any aqueous radio-isotope solution capable of being precipitated into a bioresorbable insoluble salt may be used.

The first and second solutions may be the same or different. The first and/or second solutions may be the carrier. Alternatively, the first and/or second solutions may be added to the carrier. The carrier may be heated and cooled prior to mixing with the precipitant, radio-isotope, precipitant solution, radio-isotope solution, or a combination thereof.

A visualization agent and/or a radiological indicator, such as gadolinium, barium, iodine-based contrast agent, may be optionally added to the radio-isotope solution, the precipitant solution, the carrier, or a combination thereof, preferably the precipitant solution.

In a particularly preferred embodiment, the precipitant is suspended, dispersed or dissolved in a first aqueous solution to form the precipitant solution. The precipitant solution is added to the carrier. Preferably the carrier is hydrophilic, more preferably PVOH. Radioactive ions are suspended, dispersed or dissolved in a second aqueous solution to form the radio-isotope solution. Preferably, the second aqueous solution comprises hydrogen orthophosphate. The radio-isotope solution is mixed with the carrier comprising the precipitant thereby precipitating the radioactive ions to form a plurality of insoluble radio-isotope particles dispersed within the carrier.

In other examples the radioactive ions may be adsorbed onto an anion exchange resin, and the precipitant may be applied after adsorption. In this example a precipitant such as magnesium ammonium phosphate (Struvite) may be used. In another example, a gamma source such as chromium 51 may be precipitated onto an anion exchange resin or into a resorbable radioactive molecule.

Sealed Source

The sealed source may be formed by surrounding the radioactive component with a barrier. The sealed source is bioresorbable.

In at least one embodiment the sealed source comprising a first barrier layer arranged on a first side of the sealed radioactive source and a second barrier layer arranged on a second side of the sealed radioactive source is formed by applying a radioactive component to an upper surface of the second barrier layer to provide a radioactive coated barrier layer arranging the first barrier layer above the radioactive coated barrier layer sealing the barrier layers to provide a barrier surrounding the radioactive component thereby forming the sealed radioactive source.

The lower surface of the second barrier layer may be functionalized to provide a hydrophilic surface functionalized barrier layer. Preferably, lower surface of the second barrier layer is functionalized before the radioactive coated barrier layer is formed.

Accordingly, in another embodiment the sealed source comprising a first barrier layer arranged on a first side of the sealed radioactive source and a second barrier layer arranged on a second side of the sealed radioactive source is formed by functionalizing a lower surface of the second barrier layer to provide a hydrophilic surface functionalized barrier layer applying a radioactive component to an upper surface of the second barrier layer to provide a radioactive coated barrier layer arranging the first barrier layer above the radioactive coated barrier layer sealing the barrier layers to provide a barrier surrounding the radioactive component thereby forming the sealed radioactive source.

The composition of the barrier layers may be the same or different, preferably the same. Preferably, the barrier layers comprise a biocompatible, biodegradable hydrophobic polymer. Suitable polymers include, but are not limited to: polycaprolactone (PCL), polylactide (PLA), poly(L-lactic acid) (PLLA), poly(D-lactic acid) (PDLA), poly(lactic-coglycolic acid) (PLGA), polydioxanone, caprolactone, glycolic acid, lactic acid, lactate-co-glycolate, polyurethane, and combinations thereof.

The barrier layers may be formed by any suitable method known to those in the art, including blown film extrusion, casting extrusion, and compression molding, for example after cryogrinding of raw polymer.

The barrier layers may be welded by any suitable method known to those in the art, preferably by melt sealing, to form the sealed source.

Preferably, the lower surface of the second barrier layer is functionalized to provide a hydrophilic surface functionalized barrier layer by any chemical or physical means known to those skilled in the art, including but not limited to: plasma treatment, radiation, UV crosslinking, or chemical modification such as arginine functionalization. Preferably, the lower surface of the second barrier layer is functionalized using plasma treatment with an amine monomer, such as allylamine or oxazoline, to provide an amine functionalized hydrophilic surface functionalized barrier layer. Preferably, the amine functionalized hydrophilic surface functionalized barrier layer comprises a concentration of nitrogen groups of about 5% to about 20%, including any range or value therein, including about 5%, 6%, 7%, 8%, 9%, 10%, 11%, 12%, 13%, 14%, 15%, 16%, 17%, 18%, 19%, 20%, preferably about 8%.

Adhesive Layer

A hydrophilic adhesive layer may be applied to the hydrophilic functionalized surface of the second barrier layer. Preferably, the hydrophilic adhesive layer is applied before the radioactive coated barrier layer is formed.

The hydrophilic adhesive layer may be formed by crosslinking one or more types of hydrophilic polymer precursor components. The hydrophilic polymer precursor components may comprise: polysaccharide, glycerol, starch, carboxymethyl cellulose (CM C), xylitol, citric acid, variations thereof, and combinations thereof. Preferably, the hydrophilic polymer precursor components comprise polysaccharide, carboxymethyl cellulose. Preferably the polysaccharide is pectin.

Preferably, the hydrophilic polymer precursor components are covalently bonded to the functionalized PCL barrier layer using EDC (1-ethyl-3-(3-dimethylaminopropyl) carbodiimide), NHS (N-hydroxysuccinimide).

The hydrophilic polymer precursor components may include functional groups that react with each other to form polymers.

Preferably, the hydrophilic polymer precursor components are crosslinked. Crosslinking may comprise covalent bonding, hydrogen bonding, or a combination thereof. The hydrophilic polymer precursor components may be crosslinked using: a chemical crosslinking agent, radiation, including UV and/or gamma radiation, freeze/thaw cycles, or a combination thereof.

In at least one embodiment, the hydrophilic polymer precursor components are covalently bonded to the hydrophilic functionalized surface of the second barrier layer using 1-Ethyl-3-(3-dimethylaminopropyl) carbodiimide (EDC)/N-Hydroxysulfosuccinimide sodium (NHS), dopa, or other crosslinking agent. A skilled person will understand that suitable variants thereof may be used, such as NHS, PEG-NHS. Preferably the crosslinking agent is EDC/NHS. Preferably, the NHS/EDC is provided in a ratio of about 1:1 molar, preferably about 0.001 molar to about 0.01 molar, most preferably about 0.01 molar.

In a preferred embodiment, the hydrophilic adhesive layer is formed by applying hydrophilic polymer precursor components and a crosslinking agent to the hydrophilic functionalized surface of the second barrier layer. More preferably, the hydrophilic adhesive layer is formed by applying pectin, CM C, and EDC/NHS to the hydrophilic functionalized surface of the second barrier layer to covalently bond the hydrophilic polymer precursor components to the second barrier layer, and crosslinking the hydrophilic polymer precursor components using calcium chloride or other suitable crosslinking agent. Preferably, the crosslinking is conducted at a pH of about 6.9 to about 7.5, including any range or value therein, including about 6.9, 7.0, 7.1, 7.2, 7.3, 7.4, and 7.5.

Bioresorbable Shield

The bioresorbable shield in the form of a hydrogel layer may be formed by:

suspending, dispersing or dissolving one or more types of hydrogel polymer precursor components in an aqueous solution to provide a hydrogel polymer precursor solution;

introducing porosity into the hydrogel polymer precursor solution;

drying the porous hydrogel polymer precursor solution; and covalently crosslinking the one or more types of hydrogel polymer precursor components;

thereby forming the hydrogel layer.

The hydrogel polymer precursor components may comprise: polyvinyl alcohol, forms of cellulose including but not limited to carboxymethylcellulose, varieties of collagen including but not limited to partially hydrolyzed collagen, xylitol, polyethylene glycol, polyvinylpyrrolidone, sodium alginate, starch, chitosan, glycerol, sorbitol, dextran, derivatives thereof, and combinations thereof.

The hydrogel polymer precursor components may include functional groups that react with each other to form hydrogels.

Porosity may be introduced into the hydrogel polymer precursor solution by rapidly freezing the solution to eliminate formation of large ice crystals, then freeze drying using sublimation to create porosity where the ice crystals existed.

Preferably, the hydrogel polymer precursor components are covalently crosslinked using a crosslinking agent. In a preferred embodiment, the crosslinking agent is citric acid. Preferably, the citric acid is provided in an amount of about 2 to 24%, including any range or value therein, including about 2%, 4%, 6%, 7%, 8%, 9%, 10%, 11%, 12%, 13%, 14%, 15%, 16%, 17%, 18%, 19%, 20%, 22%, 24%, most preferably about 16%.

The hydrogel may be formed by preparing a hydrogel precursor solution comprising the hydrogel polymer precursor components and crosslinking agent. The solution may be heated to any suitable temperature to initiate crosslinking depending on the precursor components and crosslinking agents used. In an embodiment where the hydrogel polymer precursor components comprise PVOH and CM C, and the crosslinking agent is citric acid, the solution is heated to about 100 to 160° C., including any range or value therein, including about 100° C., about 105° C., about 110° C., about 115° C., about 120° C., about 125° C., about 130° C., about 135° C., about 140° C., about 145° C., about 150° C., about 155° C., about 160° C., preferably about 160° C. Preferably the solution is heated for about 4 to 24 hours, including about 4 hour, about 8 hours, about 12 hours, about 16 hours, about 20 hours, about 24 hours, preferably about 16 hours.

The hydrogel precursor solution may be cast in a mold to provide a hydrogel, or a hydrogel subunit, of a desired shape and thickness. Preferably the hydrogel precursor solution is cast and dried prior to heating or initiating crosslinking. The hydrogel precursor solution may be dried at any suitable temperature to dry the solution but not initiate polymerization.

The hydrogel formed may be a single bulk layer having a thickness suitable for use as the hydrogel layer in the device, for example about 1.6 mm. The bulk layer is capable of being compressed to facilitate rolling/pressing in a delivery system whilst maintaining the ability to expand to minimum thickness of 5 mm when hydrated.

In at least one embodiment, a hydrogel subunit is formed, wherein the hydrogel subunit is in the form of a strip or sheet that may be stacked to provide the hydrogel layer for the device. The hydrogel strips or sheets preferably have a dry thickness of about 30 μm to about 1 mm (i.e., dehydrated thickness). Preferably, about 2 to 6 hydrogel strips or sheets may be stacked to provide a hydrogel layer having a thickness of about 3.5-5 mm (water equilibrium content). The stacking of plural sheets or strips allow the sheets or strips to slide relative to one another and afford flexibility of the hydrogel layer.

In a preferred embodiment, each hydrogel subunit is a porous freeze dried sheet, preferably comprising cross hatches. Each hydrogel subunit has a dried thickness of about 1 mm. The hydrogel layer comprises 2 hydrogel sheets. The hydrogel layer has a thickness of about 5 mm (water equilibrium content).

Preferably, the fenestrated hydrophobic polymer layer is in the form of a pocket, pouch or envelope to receive the hydrogel layer. The hydrophobic polymer layer is first molded in the form of a pocket, pouch or envelope, preferably by vacuum thermoform processing. Fenestrations may then be applied to the molded hydrophobic polymer layer, preferably by laser cutting, to provide the fenestrated hydrophobic polymer layer.

Device

The device may be formed by applying the bioresorbable shield to the first side of the sealed radioactive source. The bioresorbable shield may be applied to an upper surface of the first barrier layer which is arranged on the first side of the sealed radioactive source.

An upper layer may lie above the upper surface of the bioresorbable shield.

Preferably, where the bioresorbable shield is in the form of a hydrogel layer, a fenestrated hydrophobic polymer layer is applied above the upper surface of the hydrogel layer, preferably by melt welding.

In a particularly preferred embodiment, the device is formed by:

preparing a shielding assembly;
preparing a sealed radioactive source, preferably including an adhesive layer on the second side of the sealed radioactive source;
applying the shielding assembly to the first side of the sealed radioactive source; and
adhering the shielding assembly to the sealed radioactive source, preferably by melt welding
thereby providing the device.

As described above, the shielding assembly comprises the hydrogel layer, which may comprise a plurality of hydrogel subunits in the form of sheets or strips to form the hydrogel layer. A skilled person will also understand that the device may comprise one or more shielding assemblies arranged on the first side of the sealed radioactive source.

The shielding assembly may be formed by:
preparing the fenestrated hydrophobic polymer layer;
preparing the hydrogel layer;

arranging the hydrogel layer between the fenestrated hydrophobic polymer layer and a further hydrophobic polymer layer;
adhering the fenestrated hydrophobic polymer layer and the further hydrophobic polymer layer, preferably by melt welding,
thereby providing the shielding assembly.

More particularly, applying the upper surface of the hydrogel layer to the lower surface of the fenestrated hydrophobic polymer layer, applying the upper surface of the further hydrophobic polymer layer to the lower surface of the hydrogel layer.

Preferably, the sealed radioactive source, the hydrogel layer, and fenestrated hydrophobic polymer layer are sealed around an external perimeter to provide the device. The sealing at the external perimeter may occur by joining the first barrier layer, the second barrier layer and the fenestrated hydrophobic polymer layer at overlying peripheral edges. Preferably, the device includes a contrast agent in the form of gas bubbles.

One or more devices may be connected to provide a plurality of devices. Preferably each device is connected to the plurality of devices by a perforated border. This allows for one or more devices to be removed from the plurality of devices. In this way one or more devices may be administered to a subject thereby controlling the radiation dose and geometry of radioactivity delivered to the subject.

Methods of Treatment

The device of the present disclosure may be used to treat a specific localized area of the subject. The device may be suitable for minimizing and/or controlling local recurrence of tumor cells at margins of a wound site in a subject, preferably malignant cancer and seroma following cancer surgery. The device may also be suitable for minimizing and/or controlling uncontrolled growth of tumor cells at the resected margin of surgery.

In at least one aspect there is provided a method of treating a tumor, the method comprising applying into an anatomic area affected by the tumor, a device described herein. Preferably, the device is applied with the bioresorbable shield disposed upwardly relative to the anatomic area.

In another aspect there is provided a method for minimizing and/or controlling uncontrolled growth of tumor cells at margins of a wound site in a subject following surgery, the method comprising applying the device to the wound site. Preferably, the device is applied with the bioresorbable shield disposed upwardly relative to the wound site.

In at least one aspect there is provided a method of reducing tumor load in a subject, the method comprising applying into an anatomic area affected by the tumor, a device described herein. Preferably, the device is applied with the bioresorbable shield disposed upwardly relative to the anatomic area.

In at least one aspect there is provided a method of reducing the severity, or minimizing the progression, of a tumor in a subject, the method comprising applying into an anatomic area affected by the tumor, a device described herein. Preferably, the device is applied with the bioresorbable shield disposed upwardly relative to the anatomic area.

In another aspect there is provided a method for minimizing and/or controlling local recurrence of tumor cells at margins of a wound site in a subject, the method comprising applying the device to the wound site. In at least one embodiment, the method comprises minimizing and/or controlling local recurrence of malignant cancer and seroma at margins of a wound site in a subject following cancer surgery. Preferably, the device is applied with the bioresorbable shield disposed upwardly relative to the wound site.

In at least one aspect there is provided a device described herein for use in treating a tumor, comprising applying the device into an anatomic area affected by the tumor. Preferably, the device is applied with the bioresorbable shield disposed upwardly relative to the anatomic area.

In another aspect there is provided a device described herein for use in minimizing and/or controlling uncontrolled growth of tumor cells at margins of a wound site in a subject following surgery, comprising applying the device to the wound site. Preferably, the device is applied with the bioresorbable shield disposed upwardly relative to the wound site.

In at least one aspect there is provided a device described herein for use in reducing tumor load in a subject, comprising applying the device into an anatomic area affected by the tumor. Preferably, the device is applied with the bioresorbable shield disposed upwardly relative to the anatomic area.

In at least one aspect there is provided a device described herein for use in reducing the severity, or minimizing the progression, of a tumor in a subject, comprising applying the device into an anatomic area affected by the tumor. Preferably, the device is applied with the bioresorbable shield disposed upwardly relative to the anatomic area.

In another aspect there is provided a device as described herein for use in minimizing and/or controlling local recurrence of tumor cells at margins of a wound site in a subject, comprising applying the device to the wound site. In at least one embodiment, the use comprises minimizing and/or controlling local recurrence of malignant cancer and seroma at margins of a wound site in a subject following cancer surgery. Preferably, the device is applied with the bioresorbable shield disposed upwardly relative to the wound site.

In at least one aspect there is provided use of a device for treating a tumor, the use comprising applying the device into an anatomic area affected by the tumor. Preferably, the device is applied with the bioresorbable shield disposed upwardly relative to the anatomic area.

In another aspect there is provided use of a device described herein for minimizing and/or controlling uncontrolled growth of tumor cells at margins of a wound site in a subject following surgery, the use comprising applying the device to the wound site. Preferably, the device is applied with the bioresorbable shield disposed upwardly relative to the wound site.

In at least one aspect there is provided use of a device described herein for reducing tumor load in a subject, the use comprising applying the device into an anatomic area affected by the tumor. Preferably, the device is applied with the bioresorbable shield disposed upwardly relative to the anatomic area.

In at least one aspect there is provided use of a device described herein for reducing the severity, or minimizing the progression, of a tumor in a subject, the use comprising applying the device into an anatomic area affected by the tumor. Preferably, the device is applied with the bioresorbable shield disposed upwardly relative to the anatomic area.

In another aspect there is provided use of a device as described herein for minimizing and/or controlling local recurrence of tumor cells at margins of a wound site in a subject, the use comprising applying the device to the wound site. In at least one embodiment, the use comprises minimizing and/or controlling local recurrence of malignant cancer and seroma at margins of a wound site in a subject following cancer surgery. Preferably, the device is applied with the bioresorbable shield disposed upwardly relative to the wound site.

In at least one aspect there is provided a device described herein when used for treating a tumor, comprising applying the device into an anatomic area affected by the tumor. Preferably, the device is applied with the bioresorbable shield disposed upwardly relative to the anatomic area.

In another aspect there is provided a device described herein when used for minimizing and/or controlling uncontrolled growth of tumor cells at margins of a wound site in a subject following surgery, comprising applying the device to the wound site. Preferably, the device is applied with the bioresorbable shield disposed upwardly relative to the wound site.

In at least one aspect there is provided a device described herein when used for reducing tumor load in a subject, comprising applying the device into an anatomic area affected by the tumor. Preferably, the device is applied with the bioresorbable shield disposed upwardly relative to the anatomic area.

In at least one aspect there is provided a device described herein when used for reducing the severity, or minimizing the progression, of a tumor in a subject, comprising applying the device into an anatomic area affected by the tumor. Preferably, the device is applied with the bioresorbable shield disposed upwardly relative to the anatomic area.

In another aspect there is provided a device as described herein when used for minimizing and/or controlling local recurrence of tumor cells at margins of a wound site in a subject, comprising applying the device to the wound site. In at least one embodiment, the use comprises minimizing and/or controlling local recurrence of malignant cancer and seroma at margins of a wound site in a subject following cancer surgery. Preferably, the device is applied with the bioresorbable shield disposed upwardly relative to the wound site.

In at least one aspect there is provided use of a device as described herein in the manufacture of a medicament, a kit or a brachytherapy system to treat a tumor in a patient.

In another aspect there is provided a device described herein in the manufacture of a medicament, a kit or a brachytherapy system to minimize and/or control uncontrolled growth of tumor cells at margins of a wound site in a subject following surgery.

In at least one aspect there is provided use of a device as described herein in the manufacture of a medicament, a kit or a brachytherapy system to reduce tumor load in a subject.

In at least one aspect there is provided use of a device as described herein in the manufacture of a medicament, a kit or a brachytherapy system to reduce the severity, or minimize the progression, of a tumor in a subject.

In another aspect there is provided use of a device as described herein in the manufacture of a medicament, a kit or a brachytherapy system to minimize and/or control local recurrence of tumor cells at margins of a wound site in a subject, preferably, to minimize and/or control local recurrence of malignant cancer and seroma at margins of a wound site in a subject following cancer surgery.

In any embodiment, the device may be applied to a site of a surgically removed tumor.

As used herein, the term "anatomic area" refers to any part of the body of the subject, being a tissue or an organ of the body or a cavity. The term "tissue" refers to an aggregation or collection of morphologically similar cells and associated accessory and support cells and intercellular matter, including extracellular matrix material, vascular supply, and fluids. The term "organ" refers to any part of the body of an animal or of a human that is capable of performing some specialized physiological function. The term may include any part of such an organ or a collection of one or more of such organs. Non-limiting examples of organs include the heart, lungs, kidney, ureter, urinary bladder, adrenal glands, pituitary gland, skin, prostate, uterus, reproductive organs (e.g., genitalia and accessory organs), liver, gall-bladder, brain, spinal cord, stomach, intestine, appendix, pancreas, lymph nodes, breast, salivary glands, lacrimal glands, eyes, spleen, thymus, bone marrow.

The tumor may be a primary tumor. The tumor may be a metastatic or secondary tumor of a primary tumor.

The tumor may be located in any organ or tissue, and particularly those organs or tissues having relatively higher hemodynamic pressures, such as lung, liver, kidney, pancreas, bowel, sarcoma, prostate, breast and brain.

The device can be applied externally or internally. For example, the device can be inserted laparoscopically or by open surgery. The device can be used internally in the body, or externally (i.e., a skin patch). The device can be inserted into a tumor bed. For example, a tumor can be excised from a body cavity and the device can be applied to the locus thereof. The device can be fixed to the tumor bed by a variety of different methods, including adhesion, suturing, and stapling, preferably adhesion. The device can be inserted into the cavity and permitted to expand, thereby filling at least a portion of the cavity.

The device may emit a desired amount of therapeutic radiation when used in a subject.

The device may be used to treat a specific localized area in the body of a subject. The device is fabricated so that it retains the radio-isotope particles for at least a defined period of time. The device is adapted to be degraded and/or absorbed by the subject. The device is selected to disintegrate in the subject at a predetermined rate, the rate chosen depending on the half-life of the radio-isotope used in the device.

The device is eliminated by the subject over time leaving behind only a small amount of residue from the radio-isotope particles. The dissolution time is chosen to be sufficiently greater than the radioactive half-life of the radioactive material, ensuring that the remaining radioactivity due to the residue no longer poses a hazard as it migrated from the wound site. The dissolution time is chosen to be between about 6 and 10 times the half-life of the contained radio-isotope.

In a preferred use of such an embodiment, the radio-isotope particles are comprised of a material which is biocompatible, i.e., chemically inert in bodily fluids and evokes no toxic response when released into the subject, so long as the amount of radioactivity remaining in the residue is no more than about 2% of that originally present, preferably no more than about 0.1%.

In at least one aspect of the disclosure, the device is used in the treatment of diseased tissue according to the normal practice of brachytherapy in which brachytherapy sources are implanted. A type of diseased tissue which may desirably be treated by this disclosure is neoplastic tissue. Examples of diseases involving neoplastic tissue include prostate cancer, lung cancer, cervical cancer, colorectal cancer, cancer of the pancreas, breast cancer, head and neck tumors, melanomas or generally solid tumors in soft tissue. In at least one embodiment, said disease is a neoplasm, which may be benign or malignant.

The amount of radiation used in photon radiation therapy is measured in gray (Gy), and varies depending on the type and stage of cancer being treated. For curative cases, the typical biological equivalent dose ranges from about 90 to 120 Gy. M any other factors are considered by radiation oncologists when selecting a dose, including whether the patient is receiving chemotherapy, patient comorbidities, and the degree of success of surgery. An advantage of the device is that it delivers a uniform prescription dose to the wound site and minimizes dose to surrounding healthy tissues.

The choice of the radiation therapy, for example the type of radio-isotope and/or dose, can be determined by taking into consideration various factors, including, e.g., the type, size, and location of the tumor, the age, weight, and condition of the subject being treated. It is understood that the precise dose of the radiation and duration of treatment may vary with the age, weight, and condition of the subject being treated, and may be determined empirically using known testing protocols or by extrapolation from in vivo or in vitro test or diagnostic data.

In some embodiments, the device is capable of providing an absorbed radiation dose of ranging from about 90 to 145 Gy to a depth of tissue relevant for microscopic cancer cells, between about 2 and 3 mm from the lowermost surface of the device that is in contact with the wound site.

Subjects requiring treatment include those already having a benign, pre-cancerous, or non-metastatic tumor as well as those in which the occurrence or recurrence of cancer is to be prevented.

It may also be advantageous to administer the device of the present disclosure with drugs that have anti-cancer activity. Examples of suitable drugs in this regard include fluorouracil, imiquimod, anastrozole, axitinib, belinostat, bexarotene, bicalutamide, bortezomib, busulfan, cabazitaxel, capecitabine, carmustine, cisplatin, dabrafenib, daunorubicin hydrochloride, docetaxel, doxorubicin, eloxatin, erlotinib, etoposide, exemestane, fulvestrant, methotrexate, gefitinib, gemcitabine, ifosfamide, irinotecan, ixabepilone, lenalidomide, letrozole, lomustine, megestrol acetate, temozolomide, vinorelbine, nilotinib, tamoxifen, oxaliplatin, paclitaxel, raloxifene, pemetrexed, sorafenib, thalidomide, topotecan, vemurafenib, and vincristine.

The objective or outcome of treatment may be to reduce the number of, and preferably eliminate, cancer cells; inhibit (i.e., slow to some extent and preferably stop) cancer recurrence; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder.

Efficacy of treatment can be measured by assessing radiological recurrence, biochemical evidence of recurrence (for example with the use of circulating tumor markers), the duration of survival, time to disease progression, the response rates (RR), duration of response, and/or quality of life.

In at least one embodiment, the method is particularly useful for delaying disease progression.

In at least one embodiment, the method is particularly useful for extending survival of the subject, including overall survival as well as progression free survival.

In at least one embodiment, the method is particularly useful for providing a complete response to therapy whereby all signs of cancer in response to treatment have disappeared. This does not always mean the cancer has been cured.

In at least one embodiment, the method is particularly useful for providing a partial response to therapy whereby there has been a decrease in the number of cancer cells in the subject in response to treatment.

In the above described embodiments, the methods according to the disclosure may be useful for preventing doubling time of the cancer cells or otherwise inhibiting tumor growth, either through cytotoxic effect on the tumor cells or otherwise by generally inhibiting cell replication.

The disclosure may include the further step of assessing one or more organs or tissues of an individual who has received the device, to determine the regression of tumor cells or tissues in the individual. In at least one embodiment, the step utilizes radiological imaging to determine the location and volume for tumor cells or tissues in the subject after device administration. For example, this can involve three-dimensional radiological images of the subject registering geographic locations of tumor cells or tissues. Non-limiting examples of radiological images that can be used to determine location and/or volume of tumor cells or tissues include positron emission tomography (PET) scans, x-ray computerized tomography (CT), magnetic resonance imaging (MRI), nuclear magnetic resonance imaging (NMRI), magnetic resonance tomography (MRT), or a combination thereof.

In at least one embodiment, all tumor cells or tissues regress.

In another embodiment, all tumor cells or tissues are eliminated.

EXAMPLES

Brachytherapy Device

The terms "brachytherapy device" and "therapeutic patch" are used interchangeably herein. A therapeutic patch 1 according to a first embodiment of the present disclosure is shown in the cross-section in FIG. 1. As will be appreciated from a study of FIG. 1, the bottommost layer 50 of the patch 1 which is shown closest the wound site 132 will be understood as a "lower" layer of the patch 1, whereas the layer 223 will be considered an "upper" layer of the patch 1. Accordingly, this frame of reference of FIG. 1 will be used in the subsequent description. However, it will be appreciated that in use, the patch 1 may be applied to the subject in any orientation.

However, "lower" and "upper" are also used as relative terms and therefore are not only applied to layers 50 and 223 but may be used in reference to any 2 layers, when describing their relative relationship with respect to the frame of reference of FIG. 1. Furthermore, the term "outer" is used to describe features of the patch 1 when considering its structure from a plan view of the patch 1, i.e., a plan view looking down from top of the page in FIG. 1, in line with the plane of the page. For example, reference is made below to the "outer periphery" of the patch 1.

The therapeutic patch 1 includes a sealed radioactive source in the form of a pouch 59 comprising a first barrier layer 224A and a second barrier layer 224 comprised of PCL. The lower surface of the second barrier layer of PCL 224 is functionalized in the process as described below and is hydrophilic. The manufacturing method to obtain PCL layers 224 and 224A is shown in FIG. 2B and is described below as part of manufacturing process stage 200.

Sealed pouch 59 includes a radioactive component 48 that comprises a plurality of radioactive isotope particles such as Phosphorus-32 (P32) 444 dispersed within a carrier such as polyvinyl alcohol (PVOH) 40 as will be described in connection with FIG. 5D below. In particular, PVOH 40 is hydrophilic, and is not bonded to any of the surrounding PCL layers 224, 224A. PVOH 40 is instead encapsulated under vacuum within layers 224, 224A of sealed pouch 59. The radioactive component 48 is encapsulated between the layers 224, 224A of PCL to form the sealed pouch 59. As will be understood from the manufacturing description below, the sealed pouch 59 is sealed around the external periphery, in other words, sealed at or adjacent the peripheral edges. Additionally, it is possible that the two layers of PCL 224, 224A may be joined to each other in other locations, for example to form pockets of the radioactive component 48. This may increase the overall safety of the device 1 since a breach of an individual pocket may reduce the overall risk level.

As the skilled person will understand, having radioactive component 48 fully encapsulated within the pouch 59 means that the radioactive isotope 444 is fully confined or contained within the pouch. In this way, radioactive isotope 444 does not come into direct contact with the human body, either that of the subject or the theatre staff or surgeon.

Figure 5:
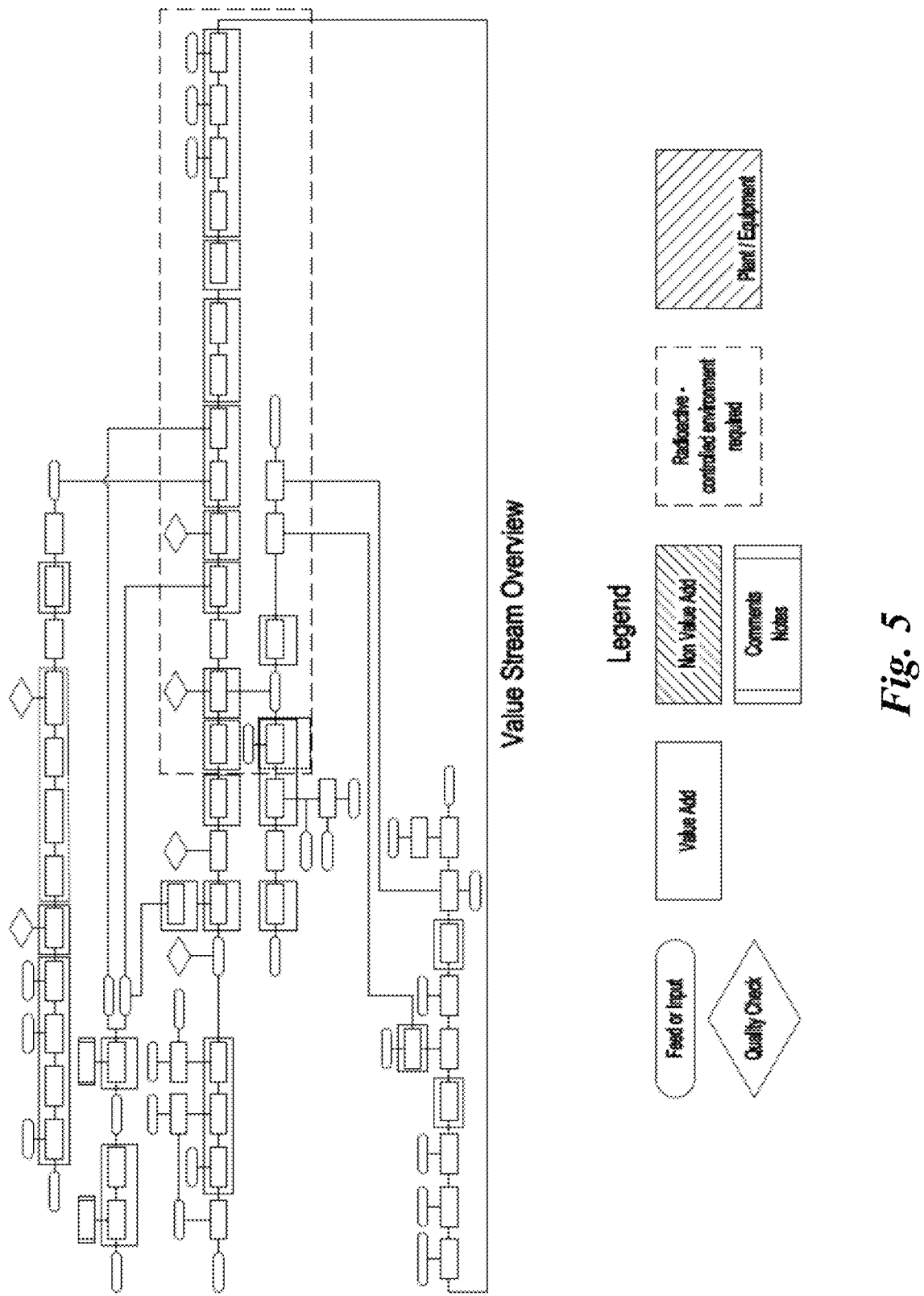
FIG. 5 is a flowchart overview entitled "manufacturing stream overview" for the flexible bioresorbable brachytherapy device according to a preferred embodiment of the present disclosure, the detail of the manufacturing method being described with reference to the Figures which follow, with a legend for the flowchart boxes.
Figure 5A:
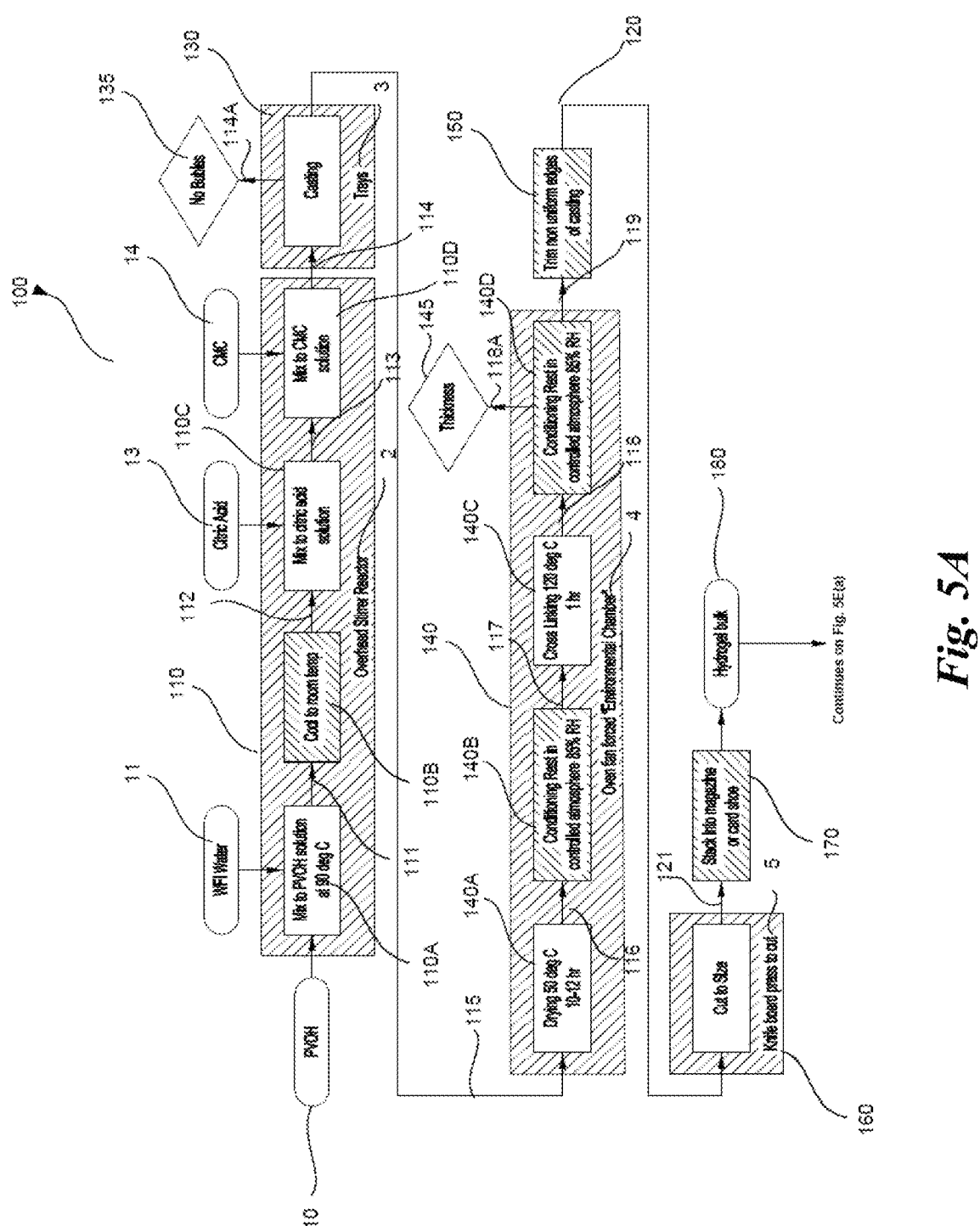
FIG. 5A is a flowchart overview of the manufacturing method to obtain hydrogel bulk or stack, forming a component of the flexible bioresorbable brachytherapy device, according to a preferred embodiment of the present disclosure.
Figure 5B:
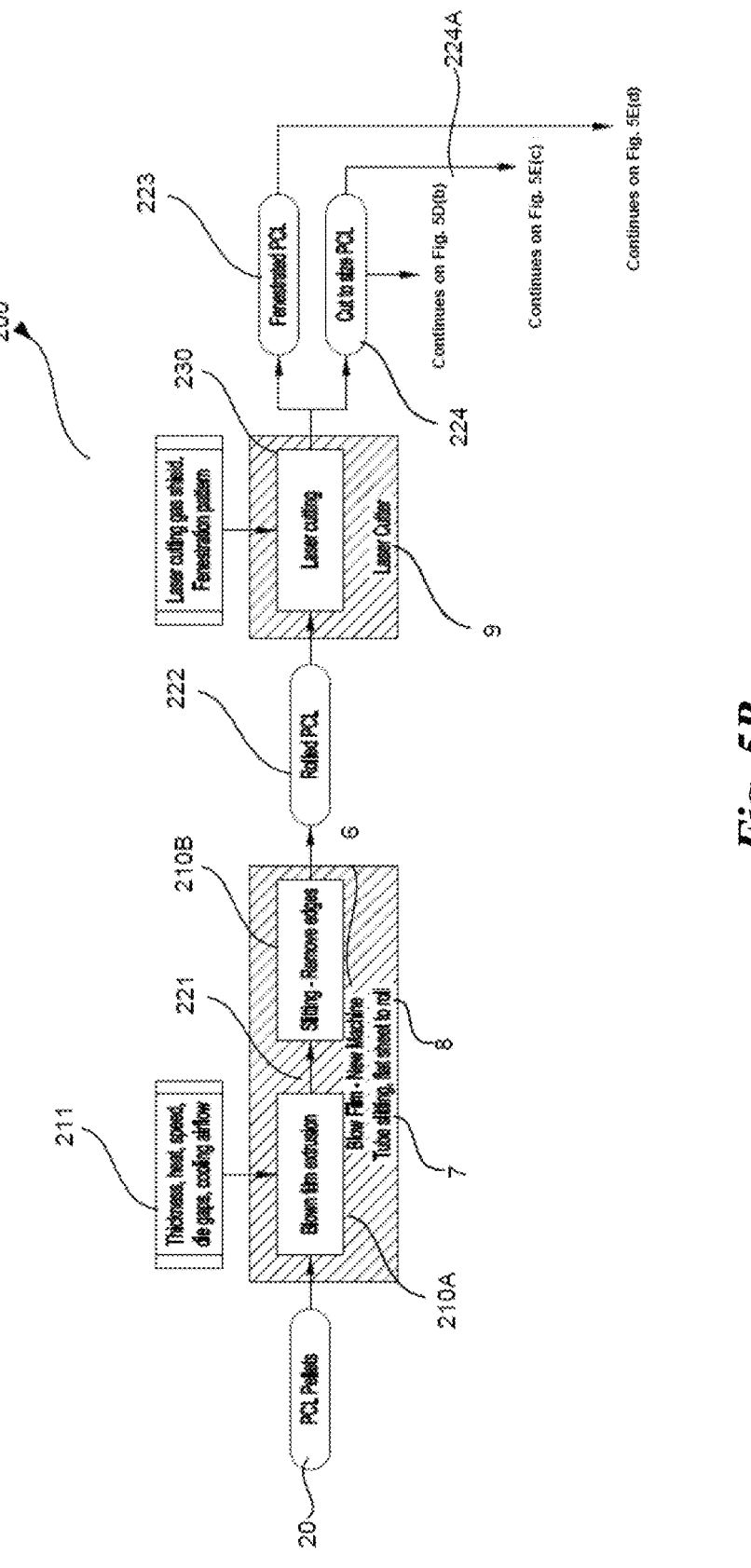
FIG. 5B is a flowchart overview of the manufacturing method to obtain PCL layers forming a component of the flexible bioresorbable brachytherapy device, according to a preferred embodiment of the present disclosure.
Figure 5C:
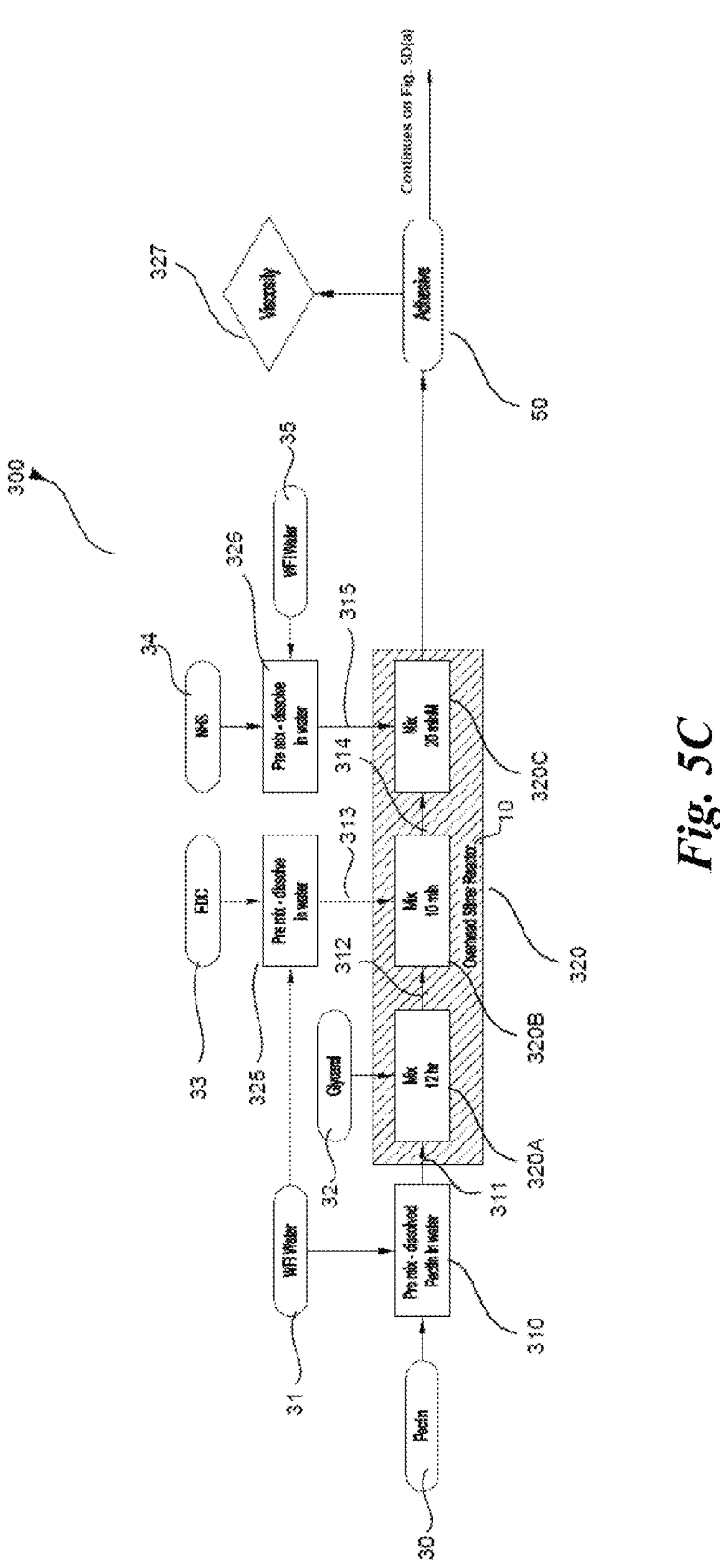
FIG. 5C is a flowchart overview of the manufacturing method to obtain a bioresorbable adhesive layer from pectin, carboxymethylcellulose, EDC (1-ethyl-3-(3-dimethylaminopropyl)carbodiimide) and a monomer with the functional group NHS (N-hydroxysuccinimide), the adhesive layer forming a component of the flexible bioresorbable brachytherapy device, according to a preferred embodiment of the present disclosure.
Figure 5D:
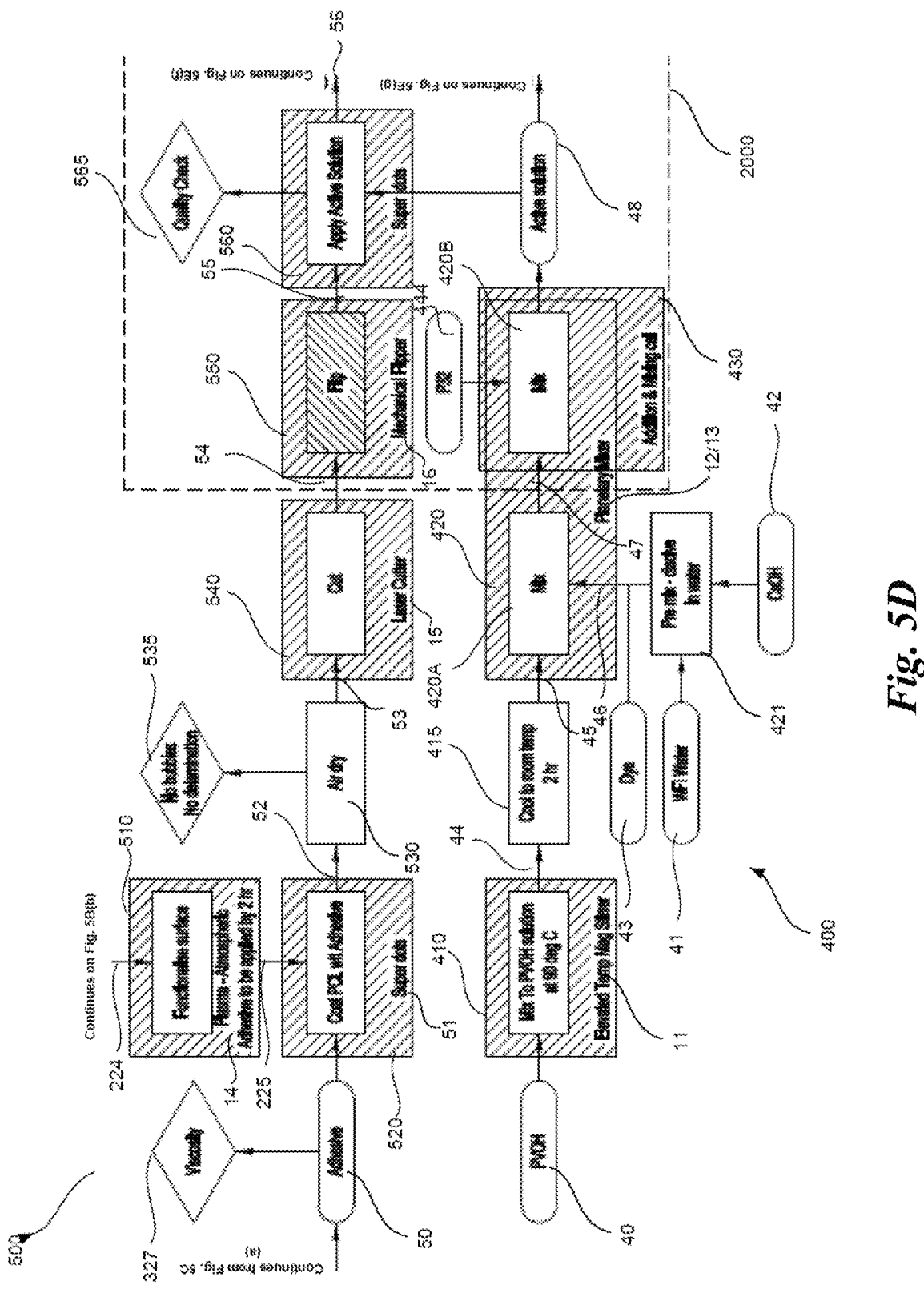
FIG. 5D is a flowchart overview of the manufacturing method to obtain a radioactive component within the sealed pouch, forming a component of the flexible bioresorbable brachytherapy device, according to a preferred embodiment of the present disclosure.

The manufacturing method to obtain radioactive component 48 is shown in FIG. 5D and described below as part of manufacturing process stage 400.

The PCL layers 224, 224A of the sealed pouch 59 are preferably configured to degrade, when implanted at the wound site, at a rate substantially longer than a half-life of the plurality of the radio-isotope particles such that the activity from the plurality of radio-isotope particles is localized to the wound site. In other words, the sealed pouch 59 acts as a sealed vessel to contain the plurality of the radio-isotope particles. Additionally, the PVOH acting as the carrier for the radio-isotopes may by configured to degrade at a rate substantially longer than a half-life of the plurality of the radio-isotope particles. Preferably, the sealed radioactive source is configured to degrade after at least six half-lives of the plurality of the radio-isotope.

As shown in FIG. 1, a hydrogel shield 180 is located above the first barrier layer of PCL 224A. The hydrogel shield 180 may be in the form of a hydrogel bulk, which may be in the form of a unitary body of hydrogel, or alternatively in the form of a multilayered stack of hydrogel strips or sheets. Preferably, the hydrogel strips or sheets may be in the form of a crosslinked foam. Foams allow for rapid hydration in vivo. The hydrogel stack 180 may be made up of 2 to 6 thin layers 121 of hydrogel strips or sheets since these thin layers slide more readily relative to one another compared to thicker layers. The dimensions of dehydrated cast hydrogel layers may be about 35 mm×45 mm×30 μm. The thickness of dehydrated crosslinked hydrogel foam layers may be about 1 mm. This arrangement imparts a greater degree of flexibility to the bulk/stack 180 than would otherwise be the case with thicker layers or a unitary body. Hydrogel shield material 180 includes carboxymethylcellulose/polyvinyl alcohol cross-linked with citric acid. The hydrogel shield material 180 may comprise or consist of that material.

The hydrogel shield 180 absorbs the radiation emitted by radioactive isotope, such as Phosphorus-32 (P32) 444, within radioactive component 48 in an upward direction away from the wound site. The hydrogel shield 180 is configured to shield radioactivity and to degrade at a rate longer than the half-life of the plurality of radio-isotope particles.

Once an aqueous solution is applied onto, or absorbed into the hydrogel bulk or stack 180, the hydrogel expands, providing a layer sufficiently thick to shield the radiation from radioactive component 48. A hydrogel layer thickness of at least about 3.5 mm (water equilibrium content) is suitable wherein the radioactive component 48 comprises beta emitter radio-isotopes. The solution may be applied to the hydrogel bulk or stack 180 by the surgeon applying for example, saline, or alternatively, the hydrogel bulk or stack 180 may absorb bodily fluids from the wound site.

In particular, the inventors have realized that the number of layers required for the hydrogel bulk 180 is defined by the number that maintains the desired thickness, in the case of beta emitter radio-isotopes at least 3.5 mm total shielding layer thickness at equilibrium water content. In a preferred embodiment, 4 to 6 stacked sheets of hydrogel are required to reduce the emitted radiation in the upward direction to within acceptable safety limits, to shield at least about 90% of the radiation to non target tissue, such that the radiation dose to non target tissue is no more than about 20-50 Gy, preferably no more than about 20 Gy.

The manufacturing method to obtain hydrogel bulk or stack 180 is shown in FIG. 5A and it is described below as part of manufacturing process stage 100.

A layer of fenestrated PCL 223 sheet is applied to the hydrogel bulk or stack 180, thus forming the uppermost layer of therapeutic patch 1. Fenestration of PCL 223 allows water into the hydrogel shielding layer. Given the radioactive source is sealed, water only penetrates the hydrogel layer and does not penetrate the radioactive sealed source.

Figure 5E:
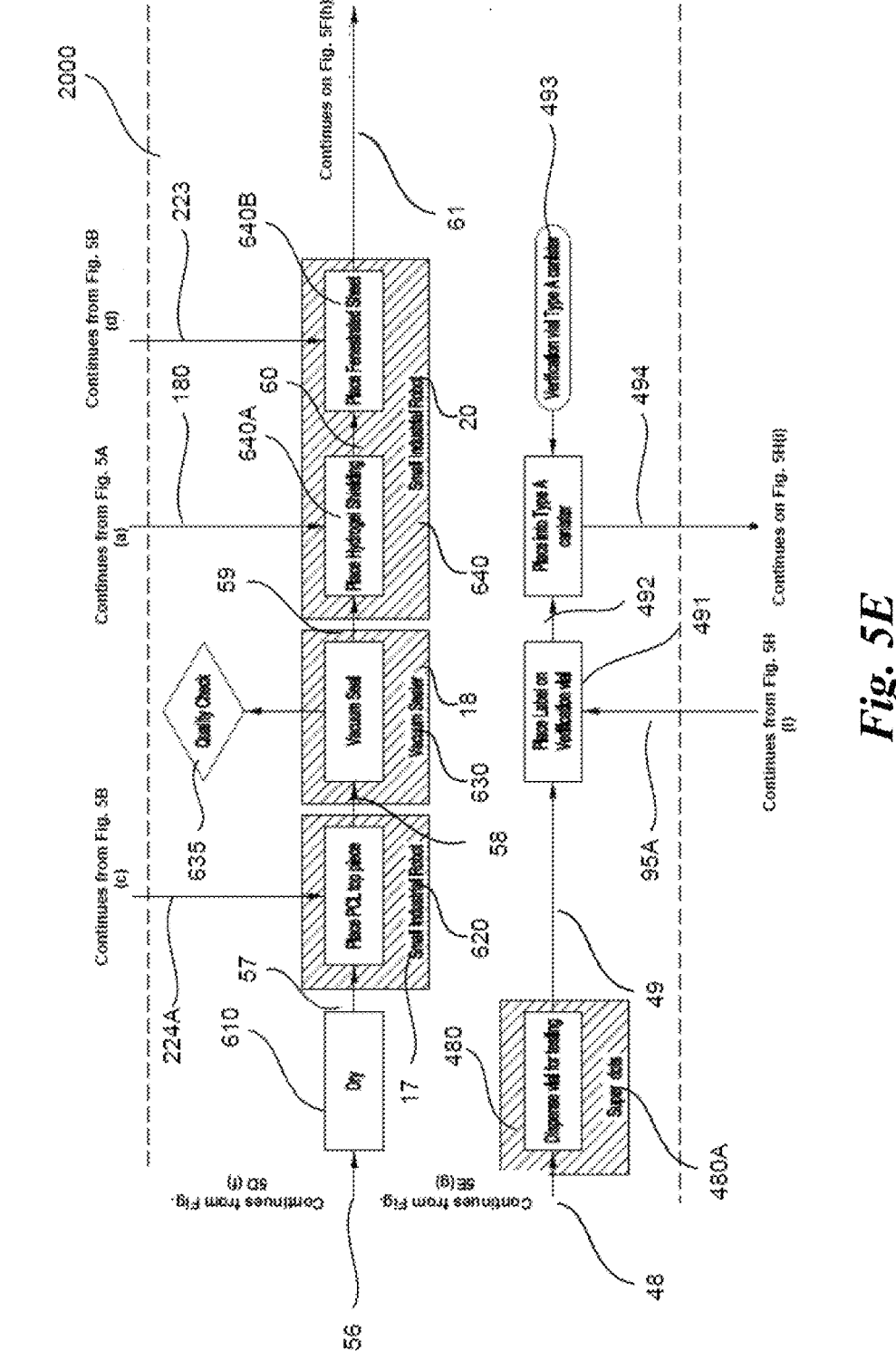
FIG. 5E is a flowchart overview of the manufacturing method to apply a fenestrated PCL layer to contain the hydrogel bulk or stack forming a component of the flexible bioresorbable brachytherapy device, according to a preferred embodiment of the present disclosure.

The manufacturing method to obtain fenestrated PCL layer 223 is shown in FIG. 5B and it is described below as part of manufacturing process stage 200. Additionally, the manufacturing method to apply fenestrated PCL layer 223 onto the hydrogel bulk or stack 180 is shown in FIG. 5E and it is described as part of manufacturing process stage 600.

Finally, in order to be able to apply therapeutic patch 1 on wound 132, hydrophilic functionalized barrier layer of PCL 224 is covalently bonded to adhesive layer 50, which is also hydrophilic.

The manufacturing method to obtain adhesive layer 50 from pectin 30 and CMC 32 is shown in FIG. 5C and it is described below as part of manufacturing process stage 200. Additionally, the manufacturing method to covalently bond adhesive layer 50 to PCL layer 224 is shown in FIG. 5D and it is described below as part of manufacturing process stage 500.

Figure 2:
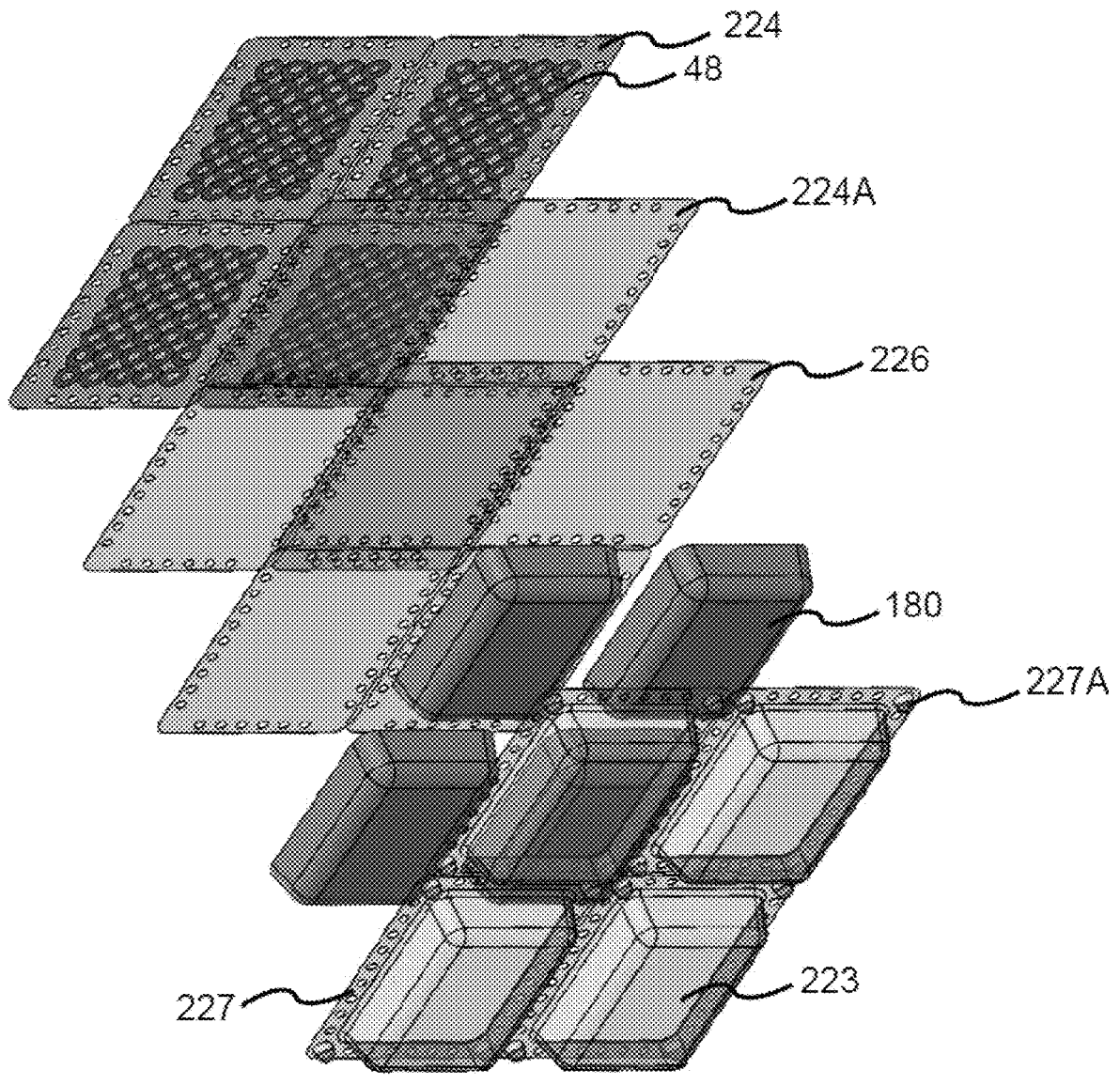
FIG. 2 is a schematic of layers of a flexible bioresorbable brachytherapy device according to a preferred embodiment of the present disclosure.
Figure 4:
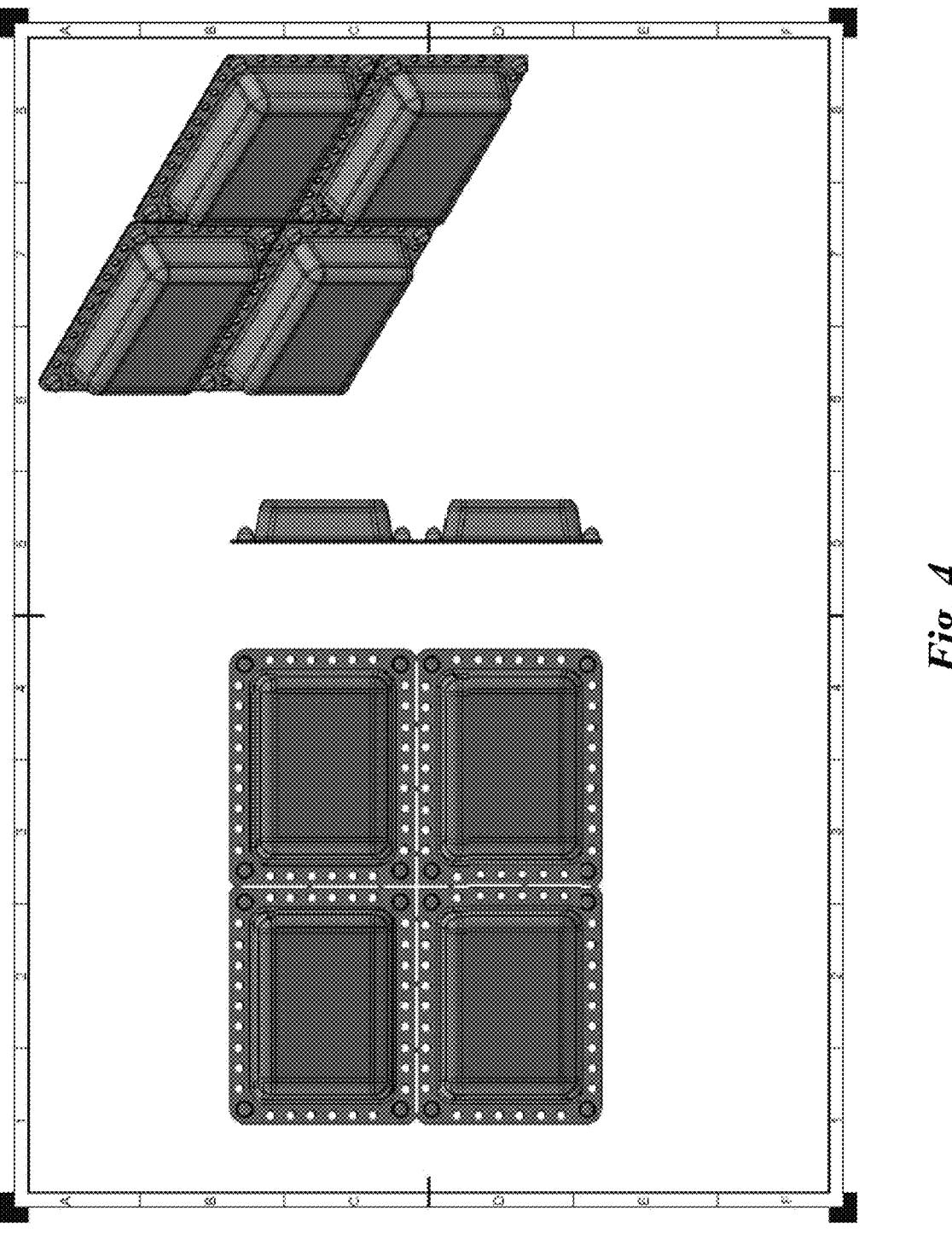
FIG. 4 is a schematic of a flexible bioresorbable brachytherapy device according to a preferred embodiment of the present disclosure.

A particularly preferred form of the disclosure is shown in FIG. 4, with the constituent layers shown in FIG. 2. The device comprises a shielding assembly and a sealed radioactive source.

Figure 3:
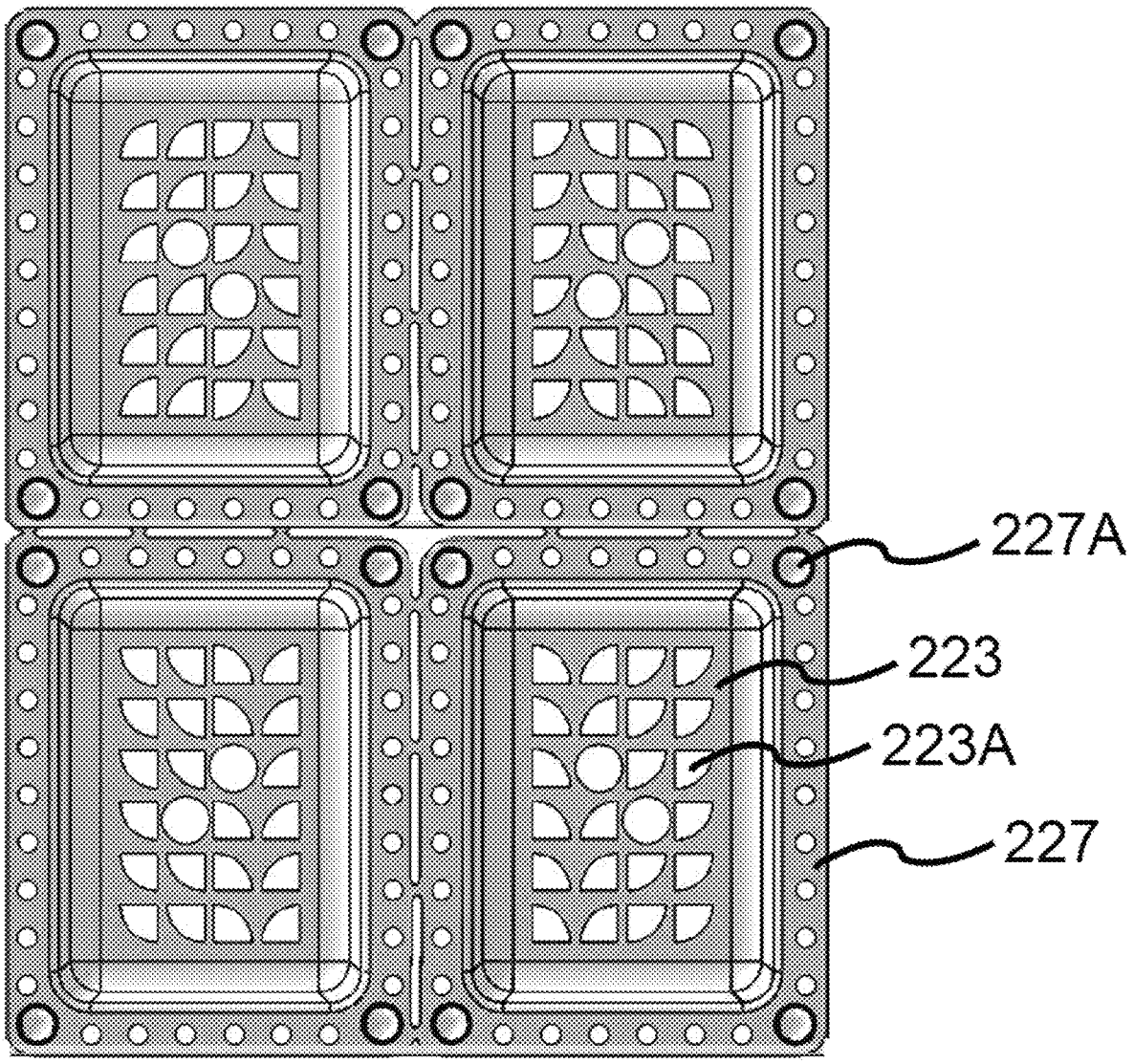
FIG. 3 is a schematic of the uppermost layer of a flexible bioresorbable brachytherapy device according to a preferred embodiment of the present disclosure.

The shielding assembly comprises an uppermost layer of fenestrated PCL 223 sheet which has been thermoform molded into a pouch to receive the hydrogel layer 180. The fenestrated PCL layer 223 is further depicted in FIG. 3, showing fenestrations 223A in the pouch region of the layer. A further hydrophobic polymer layer 226, preferably PCL, is applied to the lower surface of the hydrogel layer 180. The fenestrated PCL layer 223 and hydrogel layer 180 and further hydrophobic polymer layer 226 may be melt welded to form the shielding assembly. The peripheral edge 227 of the fenestrated PCL layer 223 may not be fenestrated. Preferably, the peripheral edges of the fenestrated PCL layer and the further hydrophobic layer are melt welded together. The peripheral edge 227 of the fenestrated PCL layer may include a negative contrast agent, preferably in the form of gas bubbles 227A as shown in FIGS. 2 and 3.

The sealed radioactive source comprises (i) a radioactive coated barrier layer comprising the radioactive component 48 applied to the upper surface of the second barrier layer 224 and (ii) a first barrier layer 224A arranged above the radioactive coated barrier layer. The barrier layers may be sealed to provide a barrier surrounding the radioactive component thereby forming the sealed radioactive source.

The shielding assembly is arranged above the first barrier layer. The sealed radioactive source and the shielding assembly may be sealed to provide the device. FIG. 2 illustrates a plurality of connected devices. The peripheral edge of each of layers 223, 226, 224A and 224 includes perforations to enable one or more devices to be removed from the plurality of devices thereby allowing for control of the number of devices and radiation dose administered to a subject.

Application of the Patch

Firstly, a tumor is surgically removed from anatomical area to provide a wound site 132 of a subject (FIG. 1) according to well understood surgical techniques. The therapeutic patch 1 may be applied to the wound site 132 from where the tumor has been surgically removed. The wound site 132 may reside internally of the subject's body, such as an internal organ or bone. Alternatively, the tissue 132 may comprise skin tissue, with the patch being applied externally of the subject's body.

Once the therapeutic patch 1 is placed on the wound site 132, the surgeon may apply an aqueous solution to the patch 1. The solution enters fenestrated PCL 223, allowing hydrogel bulk 180 to expand, for example to about 3.5 mm.

For instance, at the wound site, the therapeutic patch 1 may be applied and following, absorbable stitches may be applied to close the wound site 132. As will be understood, the surgeon carefully minimizes their own physical contact with adhesive layer 50. In order to facilitate safe application by the surgeon, an applicator may be used, as described in WO 2019/169445. However, the use of such an applicator is not essential.

Even when the tumor appears to be completely removed from anatomical area 132 after surgery, the patch 1 may still be efficacious. This is because there is a risk that cancer cells may still be present in the surrounding tissue(s), i.e., the margins of the wound. Thus, a localized radiation therapy via the therapeutic patch 1 minimizes or eliminates these remaining cancer cells, reducing the risk of tumor recurrence.

The expanded hydrogel bulk or stack 180 provides a shield for the surgeon, theatre staff and other body parts of the patient from the radiation emitted from the radio-isotope that propagates away from wound 132, i.e., upwardly and outwardly. In this way, the patient is only exposed to radiation most of which is directed in a downward trajectory towards wound 132, thus treating any residual cancer cells.

The pouch 59 provides a sealed radiation source that localizes the radiation emitted from the radio-isotope to the site of the wound 132 and minimizes radiation exposure in other body parts of the patient.

Preferably, the radio-isotope comprises a beta emitting radio-isotope with a half-life of no more than about 25 days, for example, 32-P has a half-life of about 14 days, 33-P has a half-life of about 25 days, 90-Y has a half-life of about 64 hours, 131-I has a half-life of about 8 days, 153-Sm has a half-life of about 1.9 days.

In view of the materials selected, the therapeutic patch 1 is entirely or substantially bioresorbable within the body of the patient.

Manufacturing Process and Packaging of Therapeutic Patch 1

Next, the manufacturing process to obtain and package the therapeutic patch 1 is described. This manufacturing process is shown in FIG. 5 and it includes different stages. In each stage, multiple steps and several pieces of equipment are required to prepare the various material(s) in order to achieve the final assembly of the therapeutic patch.

Hydrogel Layer

FIG. 5A shows the manufacturing process stage 100 to obtain hydrogel shield 180. The steps to obtain dry hydrogel 180 (also referred to herein as hydrogel bulk) are explained below. In some embodiments, dry hydrogel samples 180 (65×55 mm or 35×45 mm) with a mass of 1.10 g±0.2 g and thickness 1.35±0.1 mm and having uniform distribution bubbles (<1 mm diameter) are deemed to be acceptable.

In particular, as shown in FIG. 5A, manufacturing process stage 100 involves using several pieces of equipment (overhead stirrer reactor 2, oven fan forced environmental chamber 4), toolings (trays 3 and knife board press to cut 5) and multiple steps (mixing 110, casting 130, heating 140, trimming 150, die cutting 160, stacking 170). Additionally, some stages may be subject to quality control (135, 145) via short control loops. It will be understood that as production increases and more data is available, further quality check points can be added to better control production variables. The collected quality data also helps understand how to define quality measures at each step. As will be appreciated, such quality checks can be performed at any point throughout the manufacturing process.

In at least one embodiment, the hydrogel layer may be made porous by salt leaching, mechanical whisking, chemical foaming, gas instillation, freeze drying, or a combination thereof.

Each manufacturing step includes sub-steps as explained below.

Mixing 110

During mixing step 110, an overhead stirrer reactor 2 is used (FIG. 5A). Mixing may be performed using: an overhead stirrer reactor 2, or magnetic stirring with overhead stirring, preferably an overhead stirrer reactor 2. In an embodiment, an overhead stirrer with twin impeller mixing blades of 50 mm can be used to improve mixing efficiency while minimizing air entrainment into the mixture by controlling the initial mixing speed.

In particular, at sub-step 110A, the overhead stirrer reactor 2 is used to mix PVOH solution 10 with water for injection (abbrev. "WFI") 11 at 90° Celsius. Optionally, PVOH and WFI are mixed to provide a solution comprising 1-25% w/v PVOH. Optionally, PVOH and WFI are mixed at a temperature in the range 60° Celsius to 100° Celsius. Output of mixing step 110 is solution 111.

At sub-step 110B, solution 111 is cooled to room temperature to provide solution 112. Solution 112 is then mixed with citric acid 13 in mixing step 110C to provide solution 113. In some embodiments, the citric acid content in the hydrogel layer can be varied from about 2% to about 16% w/w, including any range or value therein, including about 2%, about 3%, about 4%, about 5%, about 6%, about 7%, about 8%, about 9%, about 10%, about 11% about 12%, about 13%, about 14%, about 15%, and about 16%. In an embodiment, stirring occurs for 2 minutes. In particular, in some embodiments, the final hydrogel bulk sample 180 appears to have more uniform pore structures if 10% citric acid content is used. Finally, during sub-step 110D, solution 113 is mixed with Sodium carboxymethyl cellulose (CM C) solution 14 to provide hydrogel precursor solution 114.

Casting 130

During casting 130, hydrogel precursor solution 114 is placed on trays 3. As will be understood, trays 3 are the mold that shape the hydrogel precursor solution 114 during casting 130. In an embodiment, molds are in silicon or Teflon coated aluminum.

Formation of air bubbles can occur when pouring hydrogel precursor solution 114 in trays 3. Therefore, quality test 135 may be performed with a short control loop on sample 114A, extracted from hydrogel precursor solution 114, to ensure that substantially no bubbles have formed.

The inventors observed that in both types of molds (silicon or Teflon), the hydrogel layers can shrink away from the sides of the molds and result in uneven top surfaces. The rigidity of the Teflon coated aluminum molds can cause difficulty in demolding. Silicone's flexibility can facilitate sample removal from the molds. Thus, in an embodiment, molds with one large cavity with controlled wall height to control the fill volume may be used.

The output of casting 130 is cast hydrogel precursor solution 115. After casting 130, the heating step 140 with oven fan forced environmental chamber 4 begins.

Heating 140

Heating step 140 includes multiple sub-steps (140A-D) as the inventors have realized that controlling the rate of heating and cooling is important in order to avoid unwanted effects such as surface skinning, wrinkling, splitting and tearing.

In particular, at sub-step 140A cast hydrogel precursor solution 115 is dried at 50° Celsius for a time period of about 60 minutes. Optionally, cast hydrogel precursor solution 115 is dried at a temperature in the range 50° Celsius to 130° Celsius for a time period between 30 to 90 minutes.

Subsequently, at sub-step 140B, dried hydrogel precursor 116 that is the output of heating step 140A is subject to conditioning rest at controlled atmosphere with a relative humidity of 85%. Optionally, the relative humidity is a different value in the range 80% to 90%.

After conditioning resting 140B, output conditioned hydrogel precursor 117 is cross linked during cross linking process 140C performed at 120° Celsius for 1 hour. Optionally, cross linking 140C of conditioned hydrogel precursor 117 is performed at a temperature in the range 50° Celsius to 130° Celsius for a time period between 15 minutes to 240 minutes.

Following cross linking 140C, hydrogel 118 (that is the output of cross linking step 140C) is subject to conditioning rest 140D at controlled atmosphere with a relative humidity of 85%. Optionally, the relative humidity is a different value in the range 80% to 90%.

During conditioning rest 140D, the thickness of sample 118A, extracted from hydrogel 118, may be measured with a short control loop during quality check step 145. Thickness of sample 118A can be measured with any instruments familiar to the person skilled in the art. In an embodiment, the thickness of the sample is measured using a mill gauge. In other embodiments, the thickness of the sample is measured with a transducer.

The output of heating 140 is hydrogel 119. As will be understood, care needs to be taken upon removal of the hydrogel 119 from the oven. After heating 140, the trimming step 150 begins.

Trimming 150

During trimming 150, the non-uniform edges of hydrogel 119 are removed.

The output of trimming 150 is hydrogel sheet 120. After trimming 150, the cutting step 160 begins.

Die Cutting 160

During die cutting 160, a knife board 5 is pressed on hydrogel sheet 120 to perform cutting. As the skilled reader will appreciate, many finished hydrogel layers 121 can be produced from a single hydrogel sheet 120.

Stacking 170

Finished hydrogel layers 121 are then stacked into magazine or card shoe in order to obtain hydrogel bulk or stack 180. Once obtained, hydrogel bulk 180 is then stored for later addition to the patch assembly.

Stage 100 of the process introduces the concept of tooling 'multiple cavities' as a method that can be used later on in the process to reduce exposure. The multiple cavities approach has the advantage in terms of throughput and further reduces exposure times but does add complications in terms of adding additional complexity of tooling, and due to fact that larger volumes of assemblies are handled in a shorter time. Each cavity being subtly different, and material handing required on a larger more complex scale than individual parts.

Polycaprolactone (PCL)

FIG. 5B shows the manufacturing process stage 200 to obtain PCL layers 224, 224A and fenestrated PCL 223.

In particular, as shown in FIG. 5B, manufacturing process stage 200 involves using several pieces of equipment (machine 6 including tube slitter 7 and roller 8, and laser cutter 9), and multiple steps (blown film extrusion 210A, slitting and rolling 210B, laser cutting 230).

Each manufacturing step includes sub-steps as explained below.

Blown Film Extrusion 210A

PCL pellets 20 are inserted into machine 6 to perform blown film extrusion 210A to achieve PCL film 221. Measurements on PCL film 221 such as thickness, heat, speed, die gaps and cooling airflow are required to ensure a uniform film (step 211).

In an embodiment, thickness of the film at 5 different points (Mitutoyo Absolute thickness gauge) is measured and taking an average. In an embodiment, films that have an average thickness of 50±10 micron can then be selected. Occasionally, some pinholes or bubbles can be seen on the films, but this is typically rare. On average, 7 out of 10 films pass the thickness and the surface defect analysis.

Blown PCL film 221 is then subject to slitting and rolling 210B to obtain either a uniform rolled PCL sheet 222 or two rolls of uniform PCL sheet 222 (where both edges of the blown tube are removed).

Slitting and rolling 210B allows rolled PCL 222 to be stored for future production steps.

The inventors have observed that rolled PCL 222 is stretchy and has a resiliently flexible, i.e., elastic nature and therefore it is more suitable for cutting with laser.

Laser Cutting 230

Laser cutting 230 of rolled PCL 222 is achieved by laser cutter 9. Advantageously laser cutting 230 allows development of PCL fenestration layer 223 as well as cutting PCL sheets 224 and 224A. PCL fenestration layer 223 are required to allow moisture to contact hydrogel 180 and to accommodate the expansion of the hydrogel bulk or stack 180.

Adhesive

FIG. 5C shows the manufacturing process stage 300 to obtain adhesive layer 50.

In particular, as shown in FIG. 5C, manufacturing process stage 300 involves using equipment (overhead stirrer reactor 10), and multiple steps (pre-mixing and dissolving steps 310, 325, 326, mixing 320). Additionally, quality control step 327 is also performed with a short control loop.

The above mentioned steps are discussed below.

Pre Mixing and Dissolving 310

Pectin 30 is first mixed and dissolved in WFI water 31 in step 310 at a temperature between about 50 to 90° C. The output solution 311 is placed in overhead stirrer reactor 10 where a further mixing step 320 occurs. Mixing may be performed using magnetic stirring or overhead stirring, preferably overhead stirring. In an embodiment, overhead stirrer is fitted with twin impeller mixing blades to improve mixing efficiency.

Mixing 320

Mixing 320 occurs in 3 mixing sub-steps (320A, 320B, 320C) in overhead stirrer reactor 10. During mixing sub-step 320A, output solution 311 is mixed with CMC 32. Mixing 320A occurs for 12 hours. The mix time shown in sub-step 320A is the one also used in the existing lab-based process. In an embodiment, mixing 320A can also occur for a different time duration in the range of about 3 minutes to about 3 hours.

Output 312 of mixing sub-step 320A is then mixed for 10 minutes with solution 313 during mixing sub-step 320B. Solution 313 is obtained via a pre-mixing and dissolving step 325 of 1-Ethyl-3-(3-dimethylaminopropyl) carbodiimide (EDC) 33 in WFI water 31.

The mix time (10 minutes) of sub-step 320B is the one also used in the existing lab-based process.

Output 314 of mixing sub-step 320B is mixed for 20 minutes with solution 315 during mixing sub-step 320C. Solution 315 is obtained via a pre-mixing and dissolving step 326 of N-hydroxysuccinimide (NHS) 34 in WFI water 35.

The mix time of sub-step 320C can also be used in the existing lab-based process.

Output of sub-mixing step 320C is adhesive solution 50.

Adhesive solution 50 is subject to quality control 327 with a short loop to check its viscosity. Viscosity can be measured with equipment like that found in fluids rheology. The fundamental purpose and performance of the adhesive needs to be monitored to ensure this production quality check does provide good control data.

From the results of the quality controls, the inventors have realized that the process of the present disclosure results in an adhesive 50 having improved homogeneity compared to the lab-based method.

In an embodiment, dry cured adhesive layer (110×65 mm) 50 with a mass of 1.15 g±0.2 g and thickness 0.112±0.02 mm having bubbles less have 1 mm was found to be acceptable.

The inventors realized that mixing step 320C produced a loss in the mass of adhesive layer 50. In some embodiments, the weight loss is of around 75%. In some embodiments, the inventors observed that increasing the amount of NHS 34 in solution 315 improved crosslinking and did not change the weight loss of adhesive layer 50 (of around 75%).

In an alternative embodiment, jacked reactor vessel (not shown herein) with overhead stirring and bottom take off valve can be used as overhead stirrer reactor 10 to readily prepare adhesive layer 50 at various volumes from <10 liters to 100's liters. This is an "all in one process" as the mixing and the separation can also be performed in the same vessel simply by stopping the stirring and allowing the reaction mixture to settle. Foam can rise to the top and the formulation without bubbles can be removed from the bottom of the vessel. The temperature can be controlled using external heating/cooling system and the external jacket. Additional attachments such as powder dispensing funnels may help with solid addition to the reaction vessel which will in turn assist in achieving a more homogenous mixture.

Radioactive Component

FIG. 5D (bottom) shows the manufacturing process stage 400 to obtain radioactive component 48.

In particular, as shown in FIG. 5D (bottom), manufacturing process stage 400 involves using several pieces of equipment (elevated temperature magnetic stirrer 11, planetary mixers 12 and 13), and multiple steps (mixing 410, cooling down 415, mixing 420, and additional mixing 430).

The above-mentioned steps are discussed below.

Mixing 410

During mixing step 410, Polyvinyl alcohol (PVOH) 40 is first mixed with water at 90° Celsius using elevated temperature magnetic stirrer 11.

Cool down 415

Output solution 44 is then left to cool down at room temperature for 2 hours at step 415. Optionally, cool down of output 44 occurs in a range between 24 hours to 2 weeks.

Cooled down solution 45 is then placed in planetary mixer 12 where mixing 420 takes place.

Mixing 420

During mixing sub-step 420A, solution 45 is mixed with solution 46 using planetary mixer 12. Solution 46 is obtained by pre-mixing and dissolving (Calcium hydroxide) CaOH 42 in WFI water 41. A dye 43 may optionally be added to solution 46.

Output solution 47 of mixing sub-step 420A is placed in planetary mixer 13, located in controlled environment 2000 and is mixed with Phosphorus-32 (P32) 444 during mixing sub-step 420B.

As will be understood, reduction of exposure of radioactive component 48 is a key requirement for assembly step 400.

As will be understood, the addition and mixing cell 430 can be aided through an industrial robot. In particular, the inventors are exploring the idea of a cobot (collaborative robot). Alternatively, the inventors are also considering a traditional industrial robot.

Addition and Mixing 430

Further mixing occurs during step 430. The output of mixing sub-steps 420B and 430 is radioactive component 48 containing the radioactive material P32 444.

As will be explained further below, a portion of radioactive component 48 may be used during coating step 560 using aliquots to provide a low-volume radioactive hydrogel deposit, this step forming part of the assembly process 400 (shown in FIG. 5D top).

Another portion of radioactive component 48 may be dispensed in vial for testing 480 (shown in FIG. 5E) thus achieving vial 49.

From FIG. 5E, after placing label 95A on verification vial 49 during step 491, labelled vial 492 is placed into Type A canister 493. Canister 494 containing labelled vial 492 leaves the controlled environment 2000 as it goes to the packaging stage (see FIG. 5I).

Assembly Process—Stage 500

The assembly process includes stages 500, 600, 700, 800. As will be understood, having the active material sealed inside the patch is a key requirement. This leads to the requirement of discretely creating a sealed pouch during the assembly process.

FIG. 5D (top) shows assembly process stage 500. In particular, in FIG. 5D (top), assembly process stage 500 involves using several pieces of equipment including vacuum, plasma 14, laser cutter 15, mechanical flipper 16), and multiple steps (plasma adherence 510, coating 520, drying 530, laser cutting 540, and coating 560). Additionally, some stages are subject to quality controls (535, 565)

via short control loops. Quality control 327 for adhesive 50 has been described with regards to FIG. 5C.

The above mentioned steps are discussed below.

Plasma Adherence 510

PCL sheet 224 (previously described with regards to FIG. 5B) is placed into plasma 14 either in a vacuum plasma chamber or at atmospheric pressure (See FIG. 5D) in order to functionalize its surface.

Coating 520

After approximately 2 h, functionalized PCL 225 (224A) is coated with adhesive 50 (previously described with regards to FIG. 5C) during coating step 520. Functionalized PCL 225 (224A) may be in the form of a sheet or dot 51.

Drying 530

Coated PCL 52 from coating step 520 is then dried in air during drying step 530. Formation of air bubbles in coated PCL 52 can occur. Additionally delamination of coated PCL 52 can also occur. Therefore, quality test 535 may be performed with a short control loop for coated PCL 52 before and during drying step 535 to ensure that substantially no bubbles have been formed and to check for delamination. Bubbles may be minimized using desiccation, vacuum oven, or centrifugal force using a planetary mixer.

Laser Cutting 540

Adhesive coated PCL 53 of drying step 530 is cut during step 540 using laser cutter 15. Cut, adhesive coated PCL output 54 of laser cutting 540 is then placed on mechanical flipper 16 located within controlled environment 2000.

Mechanical Flipping 550

Rotation of cut, adhesive coated PCL output 54 is achieved using mechanical flipper 15 during flipping step 550 to provide flipped, cut, adhesive coated PCL 55.

Coating 560

Flipped, cut, adhesive coated PCL 55 is then coated with active solution 48 (previously discussed). During coating 560, quality test 565 may be performed with a short control loop to ensure that active solution 48 properly adheres to the PCL output 55.

Coating step 560 provides PCL sheet or dots 56 which have been coated with active solution 48 on one surface of the PCL and coated with adhesive 50 on an opposing surface of the PCL (that had been added to functionalized PCL in step 520 as explained before).

Next, active solution 48 on PCL sheet 56 needs to be sealed by applying a top PCL sheet. The assembly process is explained below.

Assembly Process—Stage 600

FIG. 5E (top) shows assembly process stage 600. In particular, in FIG. 5E, assembly process stage 600 involves using several pieces of equipment (robot 17, vacuum sealer 18, robot 20), and multiple steps (drying 610, assembling 620, vacuum sealing 630, assembling 640). Additionally, vacuum sealing 630 may be subject to quality control (635) via a short control loop. The above-mentioned steps are discussed below.

Drying 610

During drying step 610, PCL sheet 56 (discussed in FIG. 5D) is dried. Dried PCL sheet 57 is then subject to assembling step 620.

Assembly Step 620

During assembling step 620, a small industrial Robot 17 places PCL sheet 224A (discussed in FIG. 5B) on top of on PCL sheet 57. The output is stack 58.

Vacuum Sealing 630

Stack 58 is placed into vacuum sealer 18 to remove any residual air. In particular, vacuum ensures a good perimeter seal. The output is sealed pouch 59.

Vacuum sealing step 630 may be subject to quality control (635) via a short control loop.

As will be understood, the sealing stage can explore a multi-cavity application. Multi-cavity means that many patches (multiple patches) are made in a single larger sheet, with final trimming separating the sheet into individual patches. Multi-cavity can add complication in process control but can, however, provide further reduction in exposure to technicians.

In an embodiment, an industrial robot cell can be used to reduce exposure and allow either single device handling or multi-cavity processing. The design of the robot cell is likely to be highly iterative as multiple function steps are included in the robot cell. The aim of the robot cell is to greatly reduce technician exposure times and decrease product variability.

Assembling 640

After sealed pouch 59 is produced, small industrial robot 20 places hydrogel bulk 180 on sealed pouch 59 (during step 640A). Then small industrial robot 20 places fenestrated PCL layer 223 on top of hydrogel shield to provide sealed pouch stack 60 (during assembling step 640B).

An industrial robot can be used for the stacking operations, as placing the fenestrated PCL layer 223 by hand is time consuming. Robotics at this stage also provides flexibility of stack configuration. Given the hydrogel needs to expand, configuration of the stack will become a development activity. Filling the pouch (to provide thickness in terms of shielding) while not stressing fenestration and sealing of the pouch will require design iterations.

The output of assembly sub-step 640B is assembled pouch 61.

Figure 5F:
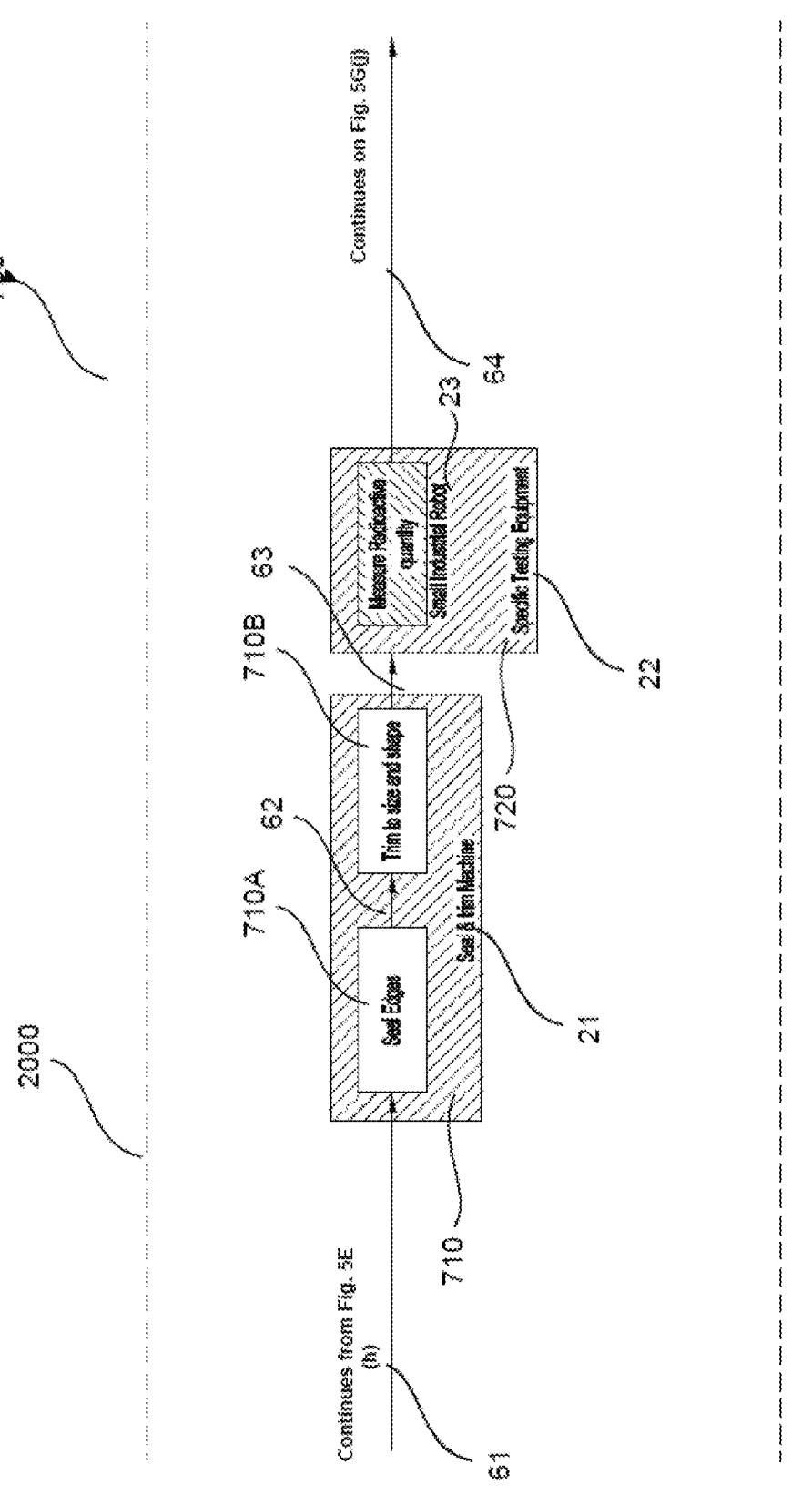
FIG. 5F is a flowchart overview for an assembly process to assemble the components of the flexible bioresorbable brachytherapy device, according to a preferred embodiment of the present disclosure.

FIG. 5F shows assembly process stage 700. In particular, in FIG. 5F, assembly process stage 700 involves using a seal and trim machine 21 during a sealing and trimming step 710. The above-mentioned step is discussed below.

Sealing and Trimming 710

Assembled pouch 61 is placed in a seal and trim machine 21 during sealing and trimming step 710. In particular, during step 710A, the edges of pouch 61 are sealed. Next, during step 710B, sealed pouch 62 is trimmed to a particular size and shape to provide patch 63. Patch 63 is the therapeutic patch 1 (shown in FIG. 1).

Testing 720

After assembly, testing 720 of patch 63 may be performed by using small industrial robot 23. The testing may be performed with specific testing equipment 22 in order to test the amount of radioactivity within patch 63.

Radioactive testing requires specialized equipment to measure. An industrial robot can be used to present the assembly to the measurement machine, reducing technician exposure.

Unique identification of the patch is required. All data such as batch parameters is required to be stored relative to this unique identification. The measurement of radioactivity, and the test vial being stored with this unique identifier and labels printed need to match up to each patch.

Packaging

Figure 5G:
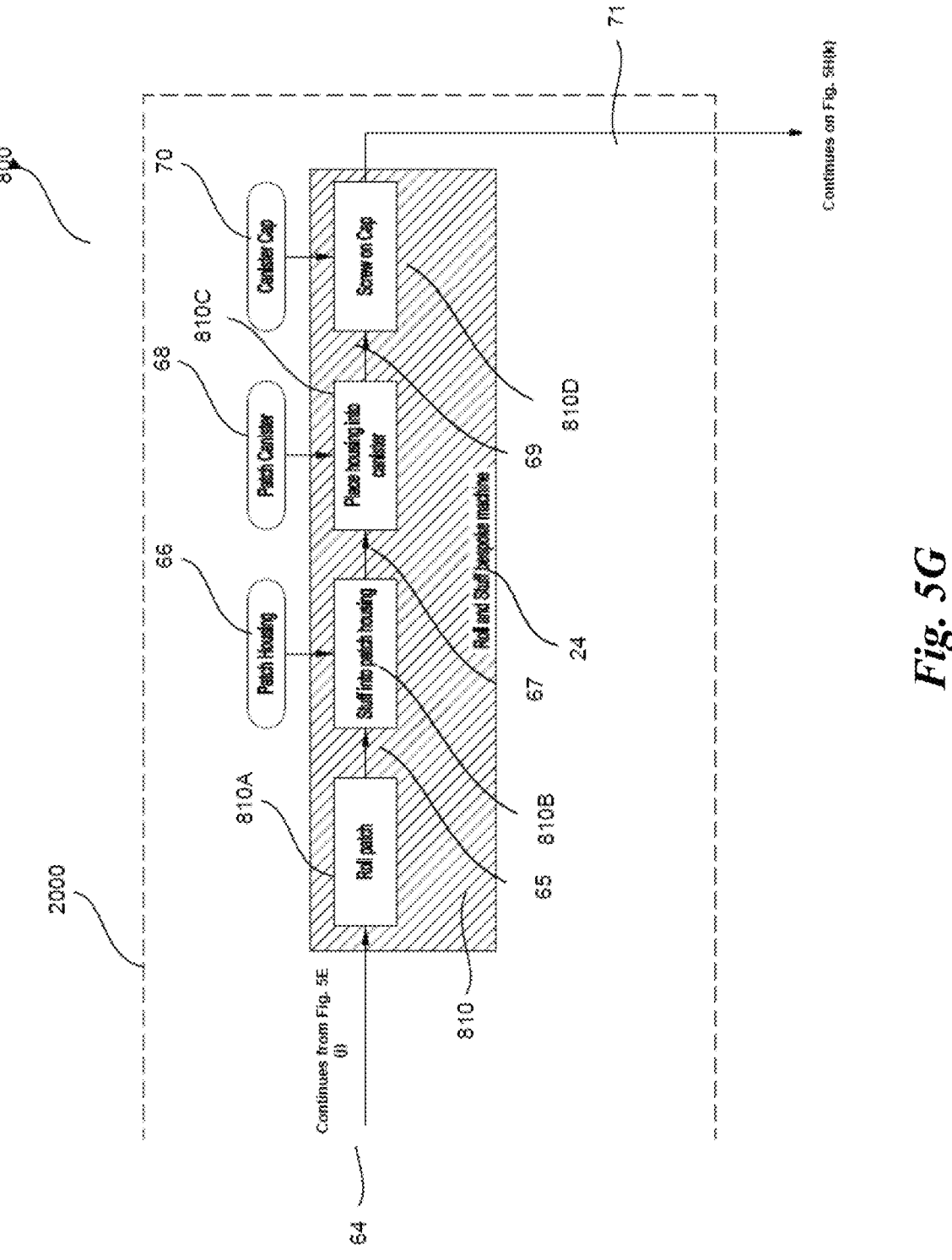
FIG. 5G is a flowchart overview for a packaging stage for the flexible bioresorbable brachytherapy device, according to a preferred embodiment of the present disclosure.

FIG. 5G shows packaging stage 800. In particular, in FIG. 5G, packaging stage 800 involves using roll and stuff bespoke machine 24 during a rolling and stuffing step 810. The above-mentioned step is discussed below.

Rolling and Stuffing 810

Rolling and stuffing 810 aims to roll and stuff patch 64 into holding canister 68.

First, during sub-step 810A, patch 64 is rolled into rolled patch 65. Next, during sub-step 810B, rolled patch 65 is stuffed into patch housing 66.

During sub-step 810C, stuffed patch housing 67 is placed into holding canister 68 to provide stuffed canister. Finally, during sub-step 810D, screw on cap 70 is placed on stuffed canister 69. Output of rolling and stuffing 810 is capped canister 71. Canister 71 includes patch housing 67.

From this point in the process exposure is managed by the canister 71 and no longer needs to be reduced for technician contact.

At the end of rolling and stuffing 810 canister 71 leaves controlled environment 2000. From this point, the canister 71 is placed into more 'traditional' packaging.

Figure 5H:
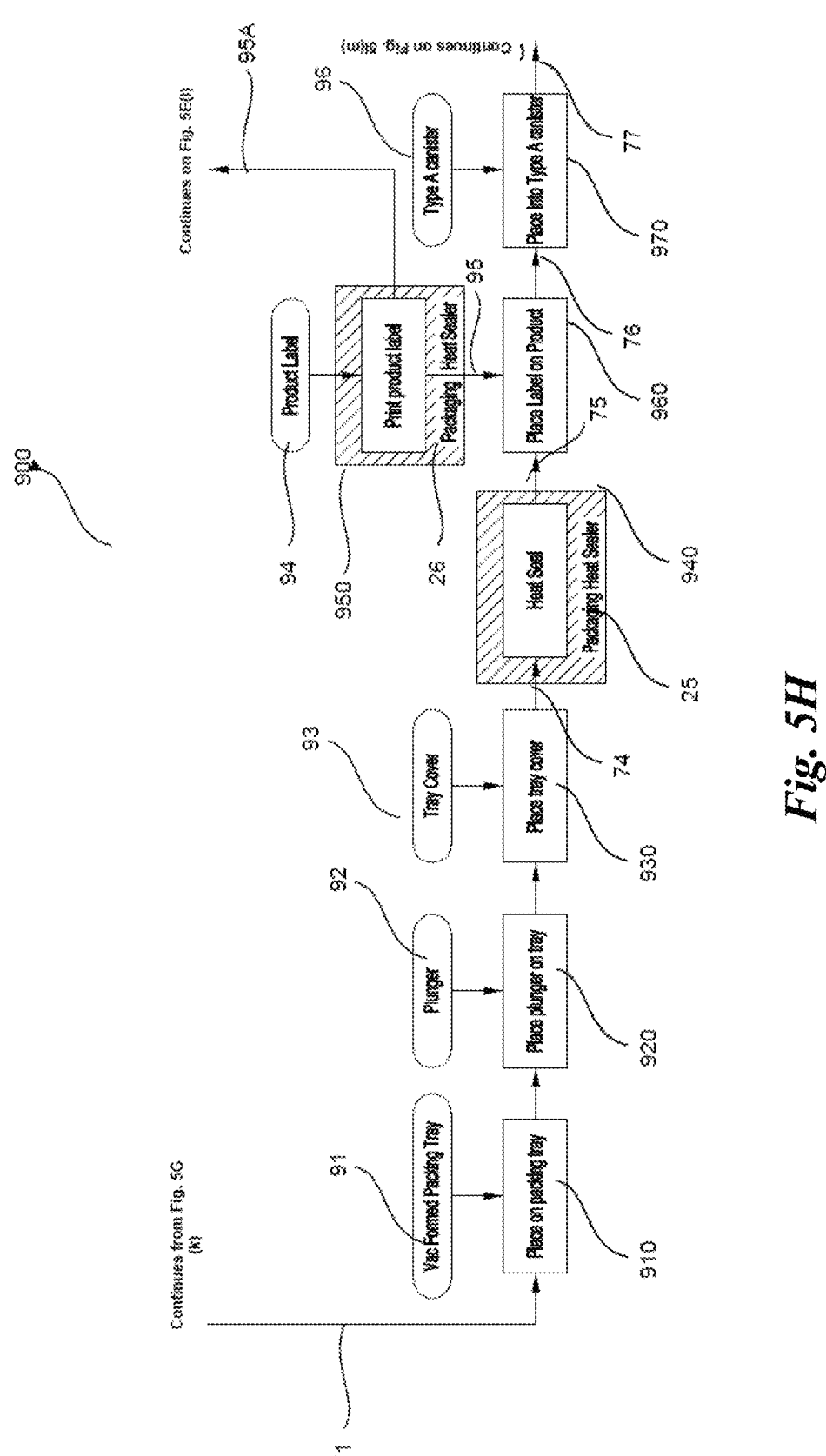
FIG. 5H is a flowchart overview of a packaging stage for the flexible bioresorbable brachytherapy device, according to a preferred embodiment of the present disclosure.

FIG. 5H shows packaging stage 900. In particular, in FIG. 5H, packaging stage 900 involves using packaging heat sealers 25, 26 during heating steps 940 and 950. Additionally, a tray is used during steps 910, 920, 930 to form kit 74. The final steps of packaging stage 900 are placing label 960 into canister 970. The above mentioned step is discussed below.

Kit on Tray 910

During step 910, canister 71 is placed on tray 91. Next, during step 920, plunger 92 is placed on the same tray. A cover 93 is then placed on the tray during step 930. At the end of step 930, the kit 74 comprises the canister 71, plunger 92, tray 91 and tray cover 93.

Heat Sealing 940

During heat sealing step 940, the kit 74 is heat sealed. The tray 91 and tray 93 are heat sealed comprising the canister 71 and plunger 92 therein. The output of heat sealing step 940 is sealed product 75.

Placing Label 960

As will be understood, a unique product label is required for each kit. In particular, each kit must contain the unique identifier of the product for traceability. Therefore, product label 94 is printed via packaging heat sealer 950. The printed label 95 is then applied, during step 960, on sealed product 75. The output of step 960 is labelled product 76.

As will be understood, a copy of the same label 95A may be placed on verification vial 49 during step 491 (shown in FIG. 5E).

Placing Canister 970

Finally, during steps 970, labelled product 76 is placed into a type A canister 96. The output is canister 77. Canister 77 includes labelled product 76.

Figure 5I:
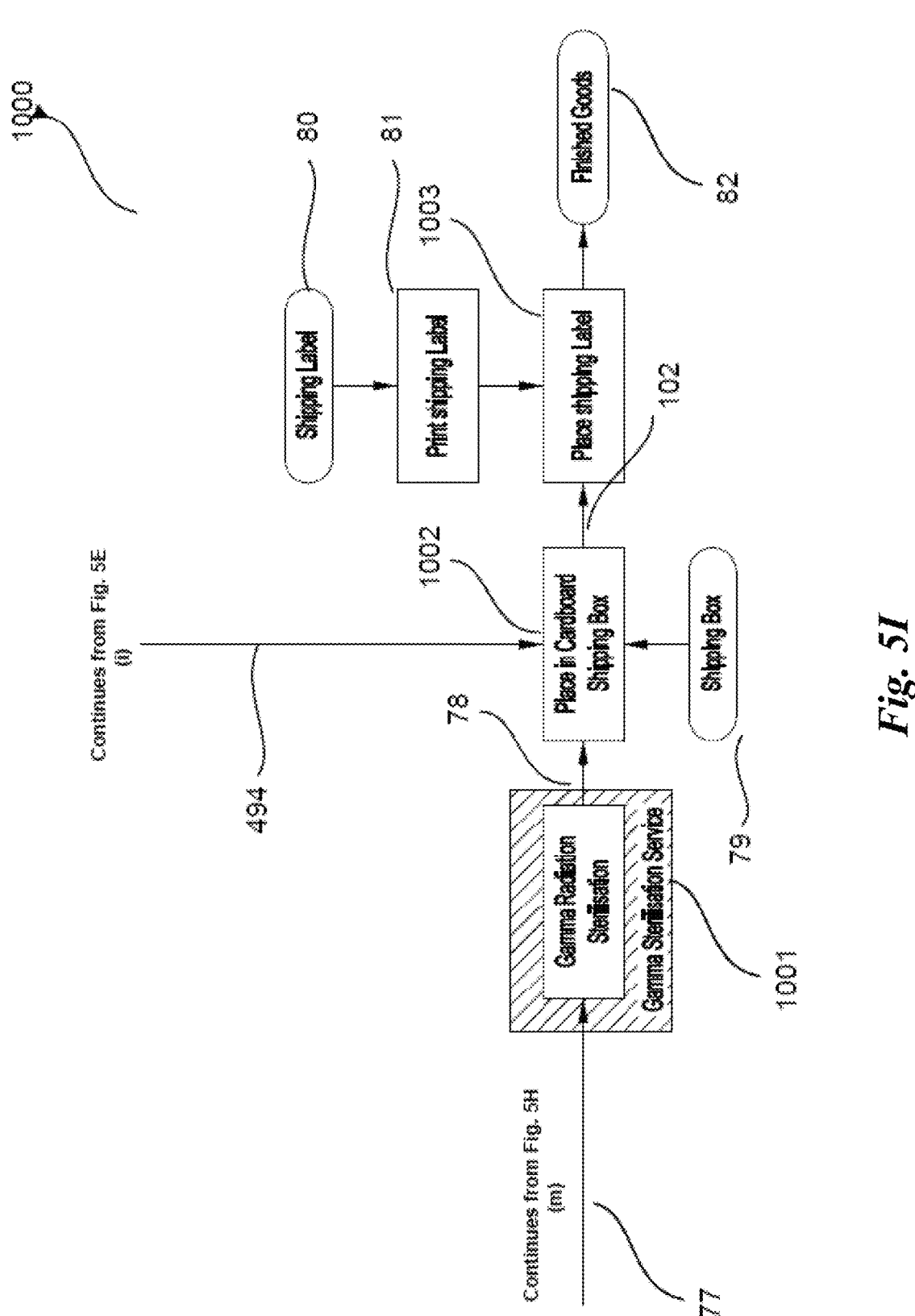
FIG. 5I is a flowchart overview of a subsequent packaging stage of the flexible bioresorbable brachytherapy device, according to a preferred embodiment of the present disclosure.

FIG. 5I shows packaging stage 1000. In particular, in FIG. 5I, packaging stage 1000 involves a Sterilization service 1001, boxing 1002 and placing a label 1003 in order to achieve finished goods 82. The above mentioned step is discussed below.

Sterilization 1001

Sterilization service 1001 of canister 77 is performed to provide sterilized product 78. Sterilization may be provided as a service by a third party prior to being placed into cardboard shipping box. Sterilization may be performed by any suitable means, including but not limited to: chemical sterilization, such as chlorine dioxide, UV, and combinations thereof.

Boxing 1002 and Placing Label 1003

Sterilized product 78 and canister 494 (discussed previously above) are then placed into cardboard shipping box 79 during boxing step 1002. Shipping label 80 is printed via printer 81 and placed on box 102 during step 1003 to provide finished goods 84.

Given the management of exposure is not critical at this point these final packaging and shipping steps can be done manually. However, if larger production volumes are required, automation can be implemented to offer support to develop the final packaging.

It will be understood that the disclosure disclosed and defined in this specification extends to all alternative combinations of two or more of the individual features mentioned or evident from the text or drawings. All of these different combinations constitute various alternative aspects of the disclosure.

The various embodiments described above can be combined to provide further embodiments. All of the patents, applications, and publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A flexible bioresorbable brachytherapy device for application on a wound site in a subject, the device comprising:
   a sealed radioactive source having opposite first and second sides, wherein the sealed radioactive source comprises:
      a radioactive component comprising a plurality of radio-isotope particles dispersed within a carrier,
      a barrier surrounding the radioactive component providing the sealed radioactive source,
      wherein the barrier functions as a barrier, when implanted at the wound site, providing the sealed radioactive source for at least six half-lives of the plurality of radio-isotope particles,
      wherein the plurality of radio-isotope particles are physically maintained in place within the sealed source such that relative movement of the plurality of radio-isotope particles is minimized for at least six half lives of the plurality of radio-isotope particles,
      a bioresorbable shield in the form of a dehydrated hydrogel layer, wherein the bioresorbable shield is located on the first side of the sealed radioactive source, the bioresorbable shield configured to shield radioactivity when implanted at the wound site for at least six half-lives of the plurality of radio-isotope particles.

2. A device according to claim 1, wherein the device comprises an adhesive layer located on the second side of the sealed radioactive source.

3. A device according to claim 1, wherein the carrier comprises a biocompatible, biodegradable insoluble hydrophilic polymer.

4. A device according to claim 3, wherein the carrier comprises a dried film of insoluble PVOH, wherein the PVOH is insoluble under physiological conditions.

5. A device according to claim 1, wherein the barrier inhibits leaching of the plurality of radio-isotope particles between the sealed source and the surrounding environment by at least about 99%.

6. A device according to claim 1, wherein the barrier comprises a biocompatible, biodegradable hydrophobic polymer.

7. A device according to claim 6, wherein the barrier comprises 80-99.9% w/v PCL.

8. A device according to claim 1, wherein the sealed radioactive source is in the form of a unified structure.

9. A device according to claim 1, wherein the second side of the radioactive source is functionalized to provide a hydrophilic surface.

10. A device according to claim 1, wherein the bioresorbable shield is configured, when implanted at the wound site, to absorb at least about 90% radiation from the sealed radioactive source for at least six half-lives of the plurality of radio-isotope particles.

11. A device according to claim 1, wherein the hydrogel layer comprises PVOH, CMC, and citric acid.

12. A device according to claim 1, wherein the device comprises a fenestrated hydrophobic polymer layer arranged above an upper surface of the hydrogel layer.

13. A method of preparing the flexible bioresorbable brachytherapy device according to claim 1, the method comprising:
   preparing a shielding assembly comprising the bioresorbable shield;
   preparing the sealed radioactive source;
   applying the shielding assembly to the first side of the sealed radioactive source; and
   adhering the shielding assembly to the sealed radioactive source to provide the device;
   wherein the shielding assembly is formed by:
      preparing a fenestrated hydrophobic polymer layer;
      preparing the dehydrated hydrogel layer;
      arranging the dehydrated hydrogel layer between the fenestrated hydrophobic polymer layer and a further hydrophobic polymer layer;
      adhering the fenestrated hydrophobic polymer layer and the further hydrophobic polymer layer to provide the shielding assembly.

14. A method for minimizing and/or controlling local recurrence of tumor cells at margins of a wound site in a subject, the method comprising applying the device according to claim 1 to the wound site.

* * * * *